(12) United States Patent
Beckers et al.

(10) Patent No.: US 12,241,082 B2
(45) Date of Patent: Mar. 4, 2025

(54) CELL CULTURING MATERIALS

(71) Applicant: KONINKLIJKE PHILIPS N.V., Eindhoven (NL)

(72) Inventors: Lucas Johannes Anna Maria Beckers, Veldhoven (NL); Jan Cornelis Kriege, Mierlo (NL)

(73) Assignee: Koninklijke Philips N.V., Eindhoven (NL)

( * ) Notice: Subject to any disclaimer, the term of this patent is extended or adjusted under 35 U.S.C. 154(b) by 759 days.

(21) Appl. No.: 16/630,872

(22) PCT Filed: Jul. 6, 2018

(86) PCT No.: PCT/EP2018/068318
§ 371 (c)(1),
(2) Date: Jan. 14, 2020

(87) PCT Pub. No.: WO2019/015988
PCT Pub. Date: Jan. 24, 2019

(65) Prior Publication Data
US 2020/0148999 A1    May 14, 2020

(30) Foreign Application Priority Data
Jul. 18, 2017   (EP) ..................................... 17181788

(51) Int. Cl.
| | |
|---|---|
| *C12N 5/00* | (2006.01) |
| *C07K 14/47* | (2006.01) |
| *C12M 1/00* | (2006.01) |
| *C12M 1/12* | (2006.01) |
| *C12M 1/42* | (2006.01) |
| *C12M 3/00* | (2006.01) |
| *C12N 5/071* | (2010.01) |
| *C12Q 3/00* | (2006.01) |
| *G16B 5/20* | (2019.01) |

(52) U.S. Cl.
CPC ........ *C12N 5/0068* (2013.01); *C07K 14/4702* (2013.01); *C12M 21/00* (2013.01); *C12M 21/08* (2013.01); *C12M 23/26* (2013.01); *C12M 23/34* (2013.01); *C12M 25/14* (2013.01); *C12M 35/08* (2013.01); *C12N 5/068* (2013.01); *C12Q 3/00* (2013.01); *G16B 5/20* (2019.02); *C12N 2506/02* (2013.01); *C12N 2506/45* (2013.01); *C12N 2533/30* (2013.01); *C12N 2533/40* (2013.01); *C12N 2533/52* (2013.01); *C12N 2537/10* (2013.01)

(58) Field of Classification Search
None
See application file for complete search history.

(56) References Cited

U.S. PATENT DOCUMENTS

| | | |
|---|---|---|
| 5,925,552 A | 7/1999 | Keogh et al. |
| 5,928,916 A | 7/1999 | Keogh |
| 6,033,719 A | 3/2000 | Keogh |
| 2009/0186411 A1 | 7/2009 | Hoffmann et al. |
| 2010/0040570 A1* | 2/2010 | Falk ........................ A61K 47/24 514/784 |
| 2010/0172856 A1 | 7/2010 | Dias et al. |
| 2010/0210745 A1* | 8/2010 | McDaniel ................ C09D 7/48 521/55 |
| 2011/0275539 A1* | 11/2011 | Spatz .................... G01N 33/552 506/13 |
| 2011/0294677 A1 | 12/2011 | Beckers et al. |
| 2020/0148999 A1 | 5/2020 | Beckers |
| 2022/0064581 A1 | 3/2022 | Van De Stolpe |

FOREIGN PATENT DOCUMENTS

| | | |
|---|---|---|
| JP | 06133766 A | 5/1994 |
| WO | 20080150947 A2 | 11/2008 |

OTHER PUBLICATIONS

Boskou et al. "Olive oil composition." Olive oil. AOCS press, 2006. 41-72 (Year: 2006).*
Fujii et al. PDMS-based microfluidic devices for biomedical applications Microelectronic Engineering 61-62 (2002) 907-914 (Year: 2002).*
Voelker et al. Functionalization of silicone rubber for the covalent immobilization of fibronectin, Journal of Materials Science: Materials in Medicine 12 (2001) 111±119 (Year: 2001).*
Huh et al "Microfabrication of human organs-on-chips" Nature Protocols vol. 8, No. 11, 2013 p. 2135-2157.
D. Bielinski et al: "Surface migration of carboxylic aciid in styrene-butacdiene rubber anid its tribological consequences", Journal of Applied Polymer Science, vol. 86, No. 13, Oct. 9, 2002 (Oct. 9, 2002), pp. 3368-3376.
S. Pinto et al: "Poly(dimethyl siloxane) surface modification with biosurfactants isolated from probiotic strains", Journal of Biomedical Materials Research. Part A, vol. 98A, No. 4,Sep. 15, 2011 (Sep. 15, 2011), pp. 535-543.
Mary L. Kraft Ft al: "Multitechnique Characterization of Fatty Acid-Modified Microgels", Langmuir, vol. 20, Jan. 22, 2004 (Jan. 22, 2004), pp. 1111-1119.
Jan Schwarz et al: "A microfluidic device for measuring cell migration towards substrate-bound and soluble chemokine gradients", Scientific Reports, vol. 6, No. 1, Nov. 7, 2016.
Liu et al Facile surface modification of silicone rubber with Zwitterionic Polymers . . . ; Materials Sience and Engineering C33 pp. 3865-3874 2013.

(Continued)

*Primary Examiner* — Kevin K Hill
*Assistant Examiner* — Alexandra F Connors

(57) ABSTRACT

A material for binding to a cell culturing protein is disclosed. The material contains a bulk-modified elastomer comprising a plurality of fatty acid moieties covalently bound to the elastomer bulk, wherein the carboxylic acid groups of said moieties are available to provide said binding. Also disclosed are a fluidic device module, a cell culturing scaffold, a fluidic device, the method of synthesizing such a material and a drug testing method. With such a material, a (monolithic) fluidic device module may be manufactured in as few as a single step injection molding process.

20 Claims, 15 Drawing Sheets

(56) References Cited

OTHER PUBLICATIONS

F. Cabrera et al "Vulcanization, centrifugation, water-washing and polymeric covering processes to Optimize . . . "; J Mater Sci 51:3003-3012 (2016).
International Search Report and Written Opinion from PCT/EP2018/068318 mailed Sep. 4, 2018.
Bielinski, D. et al., "Surface migration of carboxylic acid in styrene-butadiene rubber and its tribological consequences". Journal of Applied Polymer Science, vol. 86, No. 13 (Oct. 9, 2002), pp. 3368-3376.
Kraft, M.L. et al., "Multitechnique Characterization of Fatty Acid-Modified Microgels". Langmuir, vol. 20 (Jan. 22, 2004), pp. 1111-1119.
Schwarz, J. et al., "A microfluidic device for measuring cell migration towards substrate-bound and soluble chemokine gradients". Scientific Reports, vol. 6, No. 1 (Nov. 7, 2016).
Pinto, S. et al., "Poly(dimethyl siloxane) surface modification with biosurfactants isolated from probiotic strains". Journal of Biomedical Materials Research. Part A, vol. 98A, No. 4, (Sep. 15, 2011), Hoboken, NY, pp. 535-543.

* cited by examiner

CELL CULTURING MATERIALS

CROSS-REFERENCE TO PRIOR APPLICATIONS

This application is the U.S. National Phase application under 35 U.S.C. § 371 of International Application No. PCT/EP2018/068318, filed on Jul. 6, 2018, which claims the benefit of EP Patent Application No. EP 17181788.5, filed on Jul. 18, 2017. These applications are hereby incorporated by reference herein.

FIELD OF THE INVENTION

The present invention relates to an elastomer material for binding a cell culturing protein.

The present invention further relates to a cell culturing scaffold comprising such a material.

The present invention further relates to a fluidic device module comprising such a material.

The present invention further relates to a method of manufacturing such a material.

The present invention further relates to a drug testing method with a fluidic device module comprising such a material.

BACKGROUND OF THE INVENTION

In-vitro testing of mammalian cells or tissue is an important technique to obtain clinically important information of the mammalian material under investigation. For example, biopsied mammalian cell or tissue material may be subjected to such testing in order to determine anomalies or disease in such mammalian material or to expose diseased mammalian material to drugs, e.g. experimental drugs, to monitor the response of the diseased mammalian material to such exposure. This approach for example is frequently used in oncological procedures. This can provide important insights in how a disease in an individual can be effectively treated without having to expose the individual to a range of potentially effective drugs, which can be undesirable for a number of reasons, such as drug toxicity. In addition, the efficacy of experimental drugs for existing diseases for which no established satisfactory drug treatment is yet available may be tested in this manner. There are many other well-known reasons for deploying such in-vitro tests.

A common approach to such in-vitro testing is to immobilize the mammalian material in a fluidic device, which is sometimes referred to as an organ-on-chip. In such an approach, the mammalian material is typically immobilized on a membrane separating two fluidic channels of the fluidic device, with a first channel being used to feed the mammalian material and the second channel being used to expose the mammalian material to a chemical compound or composition of interest such as a drug treatment, e.g. to test the efficacy and/or toxicity of the drug as previously explained. The fluidic device, or at least its membrane, may be made of an elastomer such that the fluidic device may be diced or sliced in order to obtain a slice of the membrane including the mammalian material for evaluation purposes, e.g. to evaluate the reaction of the mammalian material to the exposure to the chemical compound or composition of interest.

A challenge in such in-vitro testing is to ensure that the mammalian material, e.g. cells or tissue, are stabilized and develop normally on the membrane of the fluidic device such that they live for the duration of the test procedure. This is particularly challenging in oncology procedures where experiments can be rather lengthy. To this end, the mammalian material may be stabilized using a biocompatible material such as fibronectin, which ensures that the mammalian cells will keep multiplying by providing the cells with a chemical environment mimicking that of natural tissue.

A common approach is to coat a well cell plate with a polymer having carboxylic acid groups, as such groups can (covalently) bond to the fibronectin, thereby facilitating the stabilization of the mammalian cells on the membrane within the fluidic device as the fibronectin makes the polymer bioconnective. However, this approach is not without its disadvantages. Firstly, the fluidic streams through the fluidic device may partially remove the aforementioned polymer, which compromises the ability to evaluate the mammalian material at a desired point in time due to the fact that at least some of this material may have been lost. In another approach, the membrane is treated with UV or plasma to generate binding sites for the fibronectin on the membrane. However, this approach has the drawback that it is rather difficult to avoid an inhomogeneous distribution of such binding sites, which again hampers evaluation of testing results.

Secondly, membranes comprising such a biocompatible coating are notoriously difficult to manufacture, which makes the manufacture of such fluidic devices rather costly and cumbersome. For example, such membranes typically need to be manufactured using thin-film technology, which is expensive, and need to be integrated within the fluidic device without leakage, which is far from straightforward. In addition, where the membrane itself is not made of a biocompatible material the membrane typically needs to be provided with a plurality of cell-sized holes with a small pitch to facilitate cell growth, which is also difficult to achieve.

An example of the microfabrication of such a human organ-on-chip based on thin film techniques is disclosed by Dongeun Huh et al. in Nature Protocols, Vol. 8, No. 11, 2013, pages 2135-2157. In this protocol, micro-engineering is used to fabricate a multi-layered microfluidic device containing two parallel elastomeric micro-channels separated by a thin porous flexible membrane along with two full-height, although vacuum chambers on either side, which device takes approximately 3½ days to produce. The total microfabrication procedure includes over 100 steps, with a significant number of them being critical steps. This clearly demonstrates the complexity of such manufacturing procedures. Hence, there exists a need for the provision of such a biocompatible fluidic device in a simplified manner.

SUMMARY OF THE INVENTION

The present invention seeks to provide an elastomeric material for binding to a cell culturing protein that can be used to form such a biocompatible fluidic device.

The present invention further seeks to provide a cell culturing scaffold including such an elastomeric material.

The present invention further seeks to provide a biocompatible fluidic device comprising such an elastomeric material.

The present invention further seeks to provide a method of manufacturing such an elastomeric material.

The present invention further seeks to provide a drug testing method using such a biocompatible fluidic device.

According to an aspect, there is provided a material for binding to a cell culturing protein, the material containing a bulk-modified elastomer comprising a plurality of fatty acid moieties covalently bound to the elastomer bulk, wherein the carboxylic acid groups of said moieties are available to provide said binding.

The present invention is based on the insight that such a material can be manufactured in a small number of steps, e.g. a single step in some embodiments, by combining the elastomer and the fatty acid in a coating (spin coating, dip coating, spray coating, dispensing) or an injection molding process in which the cross-linking of the elastomer with the fatty acid carbon-carbon double bond can be achieved without significant epoxidation of the fatty acid carbon-carbon double bond due to the limited exposure to ambient oxygen in the spin coating or injection molding process. Consequently, a material is provided in which the elastomer is bulk modified with fatty acid moieties in which the carboxylic acid groups of the fatty acid are available to bind to a biocompatible material. Moreover, by controlling the curing process and/or the properties of the mold in which the material is formed, such carboxylic acid groups can predominantly present on an outer surface of the material, thereby providing a substantially homogeneous distribution of carboxylic acid groups on such outer surface, which makes the material particularly suitable for use as a membrane material for a fluidic device, as each cross-section of the material will exhibit the same surface properties, in contrast to membrane materials onto which an anchor for the biocompatible material needs to be grafted or otherwise formed as previously explained. In addition, because typically only a fraction of the elastomer carbon-carbon double bonds are consumed in such a cross-linking reaction, the inventive material retains the elastomeric properties of the elastomer, which adds to the suitability of the inventive material for use in fluidic devices and facilitates the slicing or otherwise cutting of the inventive material for investigative purposes.

Preferably, each of the fatty acid moieties is covalently bound to the elastomer bulk through a cross-linking reaction between a vinyl functional group or a hydride functional group of the elastomer and an unsaturated carbon-carbon bond of an unsaturated fatty acid to ensure that the number of carboxylic acid groups available for binding to the biocompatible material can be optimized.

The unsaturated fatty acid may be any suitable unsaturated fatty acid. In an example embodiment, the unsaturated fatty acid is selected from myristoleic acid, palmitoleic acid, sapienic acid, oleic acid, elaidic acid, vaccenic acid, linoleic acid, linoeladic acid, α-linolenic acid, arachidonic acid, eicospaentaenoic acid, erucic acid and docosahexaenoic acid. Linoleic acid is specifically mentioned.

Similarly, the elastomer may be any suitable elastomer. In example embodiments, the elastomer comprises a polybutadiene backbone or a silicone backbone. Where the elastomer comprises a silicone backbone, at least a fraction of the carboxylic acid groups within the silicone backbone may be saponified as saponification of the carboxylic acid groups prior to the cross-linking between the unsaturated fatty acid molecules and the elastomer molecules may be required to prevent the cross-linking catalyst from being deactivated by the protons of the carboxylic acid groups of the unsaturated fatty acid molecules.

According to a further aspect, there is provided a cell culturing scaffold comprising the inventive material according to any of the herein described embodiments and a cell culturing protein bound to at least some of said carboxylic acid groups. Such a cell culturing scaffold can be manufactured in a straightforward manner by a simple binding reaction of the cell culturing protein to the carboxylic acid groups of the inventive material, thereby leading to a cell culturing scaffold having a substantially homogeneous distribution of cell culturing protein across a surface of the inventive material. Such a cell culturing protein for example may be selected from fibronectin, collagen and elastin although other cell culturing proteins may be contemplated.

According to yet a further aspect, there is provided a fluidic device module including a flow channel extending over a membrane, the membrane comprising the inventive material according to any of the herein described embodiments. Such a fluidic device module may comprise a first major surface comprising a first recessed structure defining a first flow channel; a second major surface opposing the first major surface and comprising a second recessed structure defining a second flow channel; with the membrane separating the first flow channel from the second flow channel. In a preferred embodiment, the fluidic device module is a monolithic fluidic device module, which has the advantage that the device module can be manufactured in a small number of processing steps, e.g. a single processing step, by injection molding.

The membrane may comprise a plurality of holes or grooves extending through the membrane. However, because the membrane may be made biocompatible by forming a cell culturing scaffold by binding to a cell culturing protein as explained above, these holes or grooves may have any suitable dimension and are not limited to cell-size dimensions, which further simplifies the manufacturing of such a fluidic device module.

In an embodiment, the first flow channel and the second flow channel are accessible through respective septums, such that the separate flow channels may be individually accessed without cross-contamination risk.

According to yet a further aspect, there is provided a fluidic device comprising the fluidic device module of any of the herein described embodiments and a pair of cover plates to fluidly seal the fluidic device module. The cover plates may be arranged such that one of said cover plates covers the first major surface, thereby sealing the first fluidic channel and the other of said cover plates covers the second major surface, thereby sealing the second fluidic channel. Such a fluidic device can be manufactured in a straightforward manner, as the fluidic device module may be formed in a small number of processing steps as previously explained, and is robust against leakage due to the flexible nature of the fluidic device module.

According to yet a further aspect, there is provided a method of manufacturing a material for binding to a cell culturing protein, the method comprising forming a composition comprising a vinyl-functionalized or hydride-functionalized elastomer or at least one precursor thereof, an unsaturated fatty acid and a cross-linking catalyst; and bulk-modifying the vinyl-functionalized or hydride-functionalized elastomer by covalently binding the fatty acid to the elastomer bulk in said mold by a cross-linking reaction between a vinyl group or hydride group of the elastomer and an unsaturated carbon-carbon bond of the unsaturated fatty acid to obtain the material. This method therefore provides a straightforward manner of providing a material that can be made biocompatible by reaction with a cell culturing protein such that the resulting cell culturing scaffold has a substantially homogeneous distribution of the cell culturing protein across a surface of the bulk-modified elastomer.

Where such a vinyl-functionalized or hydride-functionalized elastomer comprises a silicone backbone, the unsaturated fatty acid may be saponified to prevent poisoning of a cross-linking catalyst, e.g. a platinum catalyst, if present, in which case the method further comprises treating the obtained material with a protic acid to revert said saponification in order to obtain the carboxylic acid groups at least at the exposed surface of the bulk-modified elastomer.

Forming the composition comprising a vinyl-functionalized or hydride-functionalized elastomer or at least one precursor thereof, an unsaturated fatty acid and a cross-linking catalyst preferably comprises injecting the composition into a mold.

Preferably, the mold is shaped to provide the fluidic device module of any of the herein described embodiments, such that such a fluidic device module may be provided in a straightforward manner using a minimal number of processing steps. The grooves or holes in the membrane of such a fluidic device module may be formed with a laser in order to provide such grooves or holes in a straightforward manner although other techniques for forming such grooves or holes may be contemplated, such as for example by shaping the mold such that such grooves are holes are formed in the membrane of the fluidic device module during molding the module.

Such a mold preferably has a polar inner surface such a metal oxide inner surface to promote the alignment of the carboxylic acid groups of the fatty acid moieties with such an inner surface, thereby promoting the formation of a bulk modified elastomer having a high density of carboxylic acid groups on its outer surface(s).

According to still a further aspect, there is provided a drug testing method comprising providing a fluidic device module according to any of the herein described embodiments; binding the membrane of the fluidic device module to a cell culturing protein to obtain a cell culturing scaffold, applying a harvested cell culture to the cell culturing scaffold to obtain a prepared fluidic device module; form a fluidic device with the prepared fluidic device module; feeding the cell culture through one of the pair of flow channels of the fluidic device; exposing the cell culture to a drug to be tested through the other of the pair of flow channels of the fluidic device; and monitoring the response of the cell culture to the drug to be tested. Such a drug testing method can be deployed in a simple and straightforward manner, in particular in terms of preparation of the fluidic device to be used in such a drug testing method, thereby providing a significant simplification of existing drug testing methods where such fluidic devices are typically very cumbersome to prepare.

The monitoring of the response of the cell culture to the drug to be tested may comprise immobilizing and fixating the cell culture within the fluid device and slicing the fluid device module to obtain a slice for microscopic evaluation, said slice comprising at least a portion of the immobilized and fixated cell culture. In accordance with the teachings of the present invention, the generation of such slices for microscopic evaluation no longer is critical or subject to variable results due to the fact that the cell culturing scaffold is homogeneously distributed across the membrane surface of the fluidic device module.

Alternatively, in a preferred embodiment, the monitoring of the response of the cell culture may be performed within the assembled fluid device using confocal microscopy. This facilitates the real-time monitoring of such responses.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
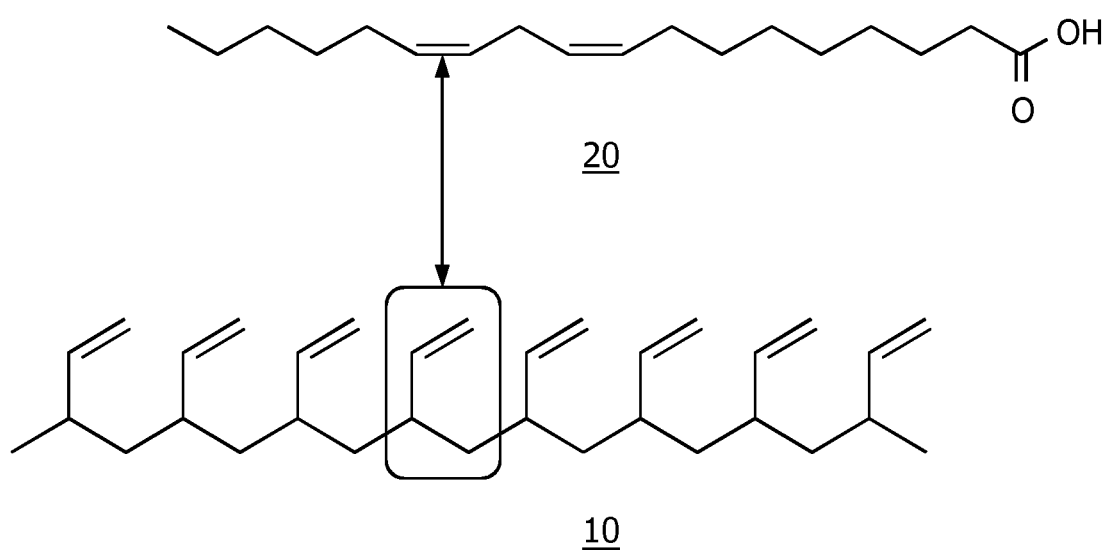
FIG. 1 schematically depicts the bulk modification of an elastomer with an unsaturated fatty acid according to an embodiment.

It should be understood that the Figures are merely schematic and are not drawn to scale. It should also be understood that the same reference numerals are used throughout the Figures to indicate the same or similar parts.

FIG. 1 schematically depicts the cross-linking reaction for producing the bulk-modified elastomer material according to embodiments of the present invention. In this cross-linking reaction, a vinyl-functionalized elastomer 10 (from here on simply referred to as elastomer) is cross-linked to an unsaturated fatty acid 20 by a cross-linking reaction between one of the carbon-carbon double bonds of the elastomer 10 and one of the carbon-carbon double bonds of the unsaturated fatty acid 20, which cross-linking reaction may be catalyzed using an appropriate cross-linking catalyst. It has surprisingly been found by the present inventors that such a cross-linking reaction can provide a bulk-modified elastomer in which the carboxylic acid groups of at least a fraction of the unsaturated fatty acid molecules 20 having engaged in the cross-linking reaction with the elastomer 10 are presented on an external surface of the bulk-modified elastomer, such that these carboxylic acid groups are available for binding reactions with cell-stabilizing (i.e. cell-culturing)

proteins such as fibronectin, collagen or elastin. This is surprising given that the elastomer 10 can be non-polar in character, in particular when the elastomer 10 is dissolved in a non-polar solvent. In such a non-polar environment, the unsaturated fatty acid molecules 20 tend to form micelles in which the carboxylic acid moieties of these molecules are turned inwardly within such micelles, which typically leads to such carboxylic acid moieties ending up within the bulk of the modified elastomer. Alternatively, the cross-linking reaction between the elastomer 10 and the unsaturated fatty acid 20 may involve the formation of a covalent bond by a reaction between a hydride functional group of the elastomer 10 and the carbon-carbon double bond of the unsaturated fatty acid 20, such as for example in the case of hydride-functionalized silicones, as will be explained in further detail below.

In addition, it is well-known per se that the carbon-carbon double bonds of such unsaturated fatty acids 20 are prone to rapid epoxidation in the presence of oxygen, which reduces the ability of such compounds to engage in cross-linking reactions with the elastomer 10.

Embodiments of the present invention are based on the insight that if a reaction mixture including the elastomer 10 and the unsaturated fatty acid 20 is brought into contact with a polar surface, this promotes orientation of the carboxylic acid groups of the fatty acid molecules along such a polar surface such that an external surface of the bulk-modified elastomer material exhibits a high density and homogeneous distribution of these carboxylic acid groups. Moreover, it has been found that when bulk modifying the elastomer 10 in this manner in an injection molding process at elevated temperatures, e.g. temperatures in a range of 120-240° C., epoxidation of the carbon-carbon double bonds of the unsaturated fatty acid molecules 20 does not significantly interfere with the bulk modification of the elastomer 10, i.e. does not significantly inhibit the cross-linking reaction between the unsaturated fatty acid molecules 20 and the elastomer 10. Without wishing to be bound by theory, it is believed that in such injection molding processes, molecular oxygen is largely absent from the reaction mixture within the injection molding apparatus, thereby suppressing the unwanted epoxidation of these carbon-carbon double bonds.

The mold used in such an injection molding process may be shaped in the form of a fluidic device module such that a monolithic fluidic device module may be formed in a single step injection molding process. Due to the high density and homogeneous distribution of carboxylic acid groups on the external surface(s) of such a monolithic fluidic device module, such a device module can be made biocompatible in a straightforward manner by binding a cell-culturing protein such as fibronectin, collagen or elastin to the exposed carboxylic acid groups on the external surface of the bulk-modified elastomer. The mold may be made of or have an inner surface coated with any suitable polar material, such as stainless steel, a metal or a metal oxide such as aluminium oxide in order to achieve the desired orientation of the carboxylic acid groups of the bulk-modified elastomer on at least one of its external surfaces.

Any suitable elastomer may be used for this purpose. For example, the elastomer may be a homopolymer, a copolymer, a block copolymer, a terpolymer, a block terpolymer and so on. A particularly suitable elastomer may be selected from polyenes such as polybutadiene. Where polybutadiene is used, the polybutadiene may be made using any suitable polymerization process. Particularly preferred is a polybutadiene formed in a Nd or Li-catalyzed polymerization reaction, as it is well-known per se that such polybutadiene has a low degree of branching (typically below 5%) and a low degree of polydispersity (Mw/Mn) of around 2. Li-catalyzed polybutadiene is particularly preferred due to its high degree of 1,2-vinyl content (about 11%). However, other types of polybutadiene, e.g. polybutadiene obtained from a Co, Ni or Ti-catalyzed polymerization reaction may be used instead. Where a polyene such as polybutadiene is used as the elastomer 10, the cross-linking reaction between the elastomer 10 and the unsaturated fatty acid 20 may be catalyzed using a peroxide catalyst. In another advantageous embodiment, a Li-catalyzed polybutadiene is used having a degree of branching in a range of 5-15% as it has been found that when the degree of branching of the polybutadiene is in this range, the reactivity of the polybutadiene with the unsaturated fatty acid 20 is improved. It is noted for the sake of completeness that it is well-known per se how to control the degree of branching when synthesizing polybutadiene such that this will not be further explained for the sake of brevity only.

Another class of elastomer is that are specifically mentioned is silicones (polysiloxanes) for injection molding. Such silicones may comprise a PDMS backbone including vinyl moieties to facilitate cross-linking through Pt-catalyzed addition reactions, e.g. with (poly methyl) hydrogen siloxanes. Instead of or in addition to such cross-linking with (poly methyl) hydrogen siloxanes, the vinyl-functionalized PDMS backbone may be cross-linked with unsaturated fatty acids 20. Such silicones may be formed by a cross-linking reaction between a vinyl-functionalized linear or branched silicone monomer or oligomer, e.g. a T-branched or Q-branched silicone monomer or oligomer and a linear hydride-functionalized silicone monomer or oligomer, between a hydride-functionalized linear or branched silicone monomer or oligomer, e.g. a T-branched or Q-branched silicone monomer or oligomer and a linear vinyl-functionalized silicone monomer or oligomer or mixtures of vinyl-functionalized and hydride-functionalized linear or branched silicone monomers or oligomers, e.g. a T-branched or Q-branched silicone monomer or oligomer and/or a mixture of linear hydride-functionalized and vinyl-functionalized silicone monomer or oligomer.

For example, the two-component silicone may be formed by a cross-linking reaction between a linear component 1 and a linear component 2, which each may correspond to the general formula below:

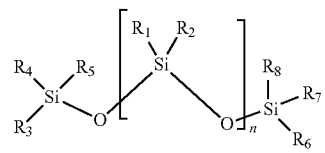

In component 1, $R_1$ and $R_2$ are individually selected from $C_1$-$C_3$ alkyl, $R_3$-$R_8$ are individually selected from $C_1$-$C_3$ alkyl and vinyl, with the proviso that at least one of $R_3$-$R_5$ and at least one of $R_6$-$R_8$ is vinyl. Preferably, at least three of $R_3$-$R_8$ are vinyl. In all embodiments, n may be in the range of 100-200,000. In a specific embodiment of component 1, each of the groups $R_1$-$R_8$ that is an alkyl group is a methyl group, i.e. the component 1 is vinyl-functionalized PDMS having terminal vinyl groups.

In component 2, $R_1$ is hydrogen, R2=$C_1$-$C_3$ alkyl and $R_2$-$R_8$ are individually selected from $C_1$-$C_3$ alkyl or hydrogen, with the proviso that at most one of $R_3$-$R_5$ and at most one of $R_6$-$R_8$ is hydrogen, and and n may have any suitable value, such as n=3-1,000 or more specifically n=3-10. In a specific embodiment of component 2, none of the groups $R_3$-$R_8$ are hydrogen. In another specific embodiment of component 2, each of $R_2$-$R_8$ are methyl.

Component 2 typically acts as a cross-linking agent for component 1. Such cross-linking reactions, which are typically Pt-catalyzed, are well-known per se, see for example WO 2009/147602 A2 and are therefore not explained in further detail for the sake of brevity. Any suitable silicone elastomer may be used. It should be understood that when cross-linking such silicones in the presence of an unsaturated fatty acid 20, the covalent bond between the silicone and the unsaturated fatty acid 20 alternatively may be formed by a reaction between a hydride functional group of the (cross-linked) silicone and the unsaturated fatty acid 20 as suggested in the below reaction mechanism:

material that is highly permeable to water and other compounds (e.g. drugs) is obtained that facilitates maximized perfusion of these compounds into the cells on the membrane of the fluidic device module 100. However, where real-time monitoring of drug consumption by cells is desirable, a polyene-based material such as a polybutadiene-based material that is non-permeable to water and drugs may be preferable, as the rate of perfusion of these compounds to the cells can be controlled using the density of apertures through the membrane.

In an embodiment, the polysiloxane may be formed from a multi-component starting material as previously explained in order to prevent premature cross-linking of the polysiloxane. Such multi-component starting materials are well-known per se; for example, such multi-component starting

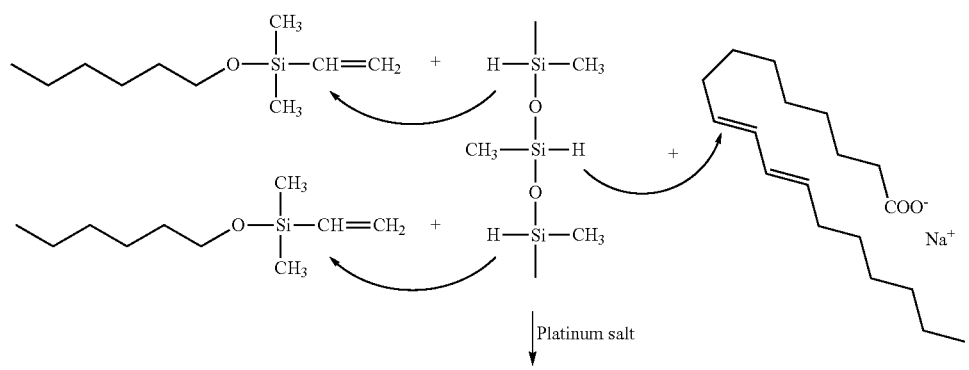

In order to prevent catalyst inhibition by the protons of the carboxylic acid groups of the unsaturated fatty acids 20 during such cross-linking reactions, the unsaturated fatty acid may be used in a saponified form in the cross-linking reaction with a silicone elastomer, e.g. as the sodium salt of such an unsaturated fatty acid, with the cross-linking reaction product subsequently being treated with a strong protic acid, e.g. HCl or the like, in order to reinstate the carboxylic acid groups on the surface of the bulk-modified elastomer. In this embodiment, a fraction of the fatty acid moieties within the bulk of the bulk-modified elastomer may remain saponified due to the fact that the protic acid may be unable to reach the bulk due to the length of the diffusion channels between the surface of the bulk-modified elastomer and its bulk. As will be readily understood, this is not a problem given that the bulk-modified elastomer can still be made biocompatible due to the availability of the carboxylic acid groups on one or more of its surfaces. Any suitable type of polysiloxane may be used for this purpose.

Alternatively, a silicone backbone such as a (poly methyl) hydrogen siloxane backbone may be crosslinked with rubber-like polymers such as polybutadiene and polyisoprene, with the unsaturated fatty acid being incorporated in such a crosslinked product. This for example may be done to tune the water permeability of the final material as silicones typically have a rather open structure whilst such rubber-like polymers have a rather closed structure, such that the openness, i.e. the water permeability, of the crosslinked product can be tuned by the ratio of silicone and rubber-like polymer therein. In this manner, the properties of the material according to this embodiment may be optimized for cell/protein interaction to build good scaffolds. For example, where the elastomer is a silicone-based, e.g. PDMS-based, a material kits are marketed by Wacker Chemie AG from Munich, Germany under the tradename Elastosil.

Regarding to unsaturated fatty acid 20, any suitable unsaturated fatty acid may be used for the purpose of cross-linking it with the elastomer 10. For example, the unsaturated fatty acid 20 may be selected from myristoleic acid, palmitoleic acid, sapienic acid, oleic acid, elaidic acid, vaccenic acid, linoleic acid, linoeladic acid, α-linolenic acid, arachidonic acid, eicospaentaenoic acid, erucic acid and docosahexaenoic acid. Linoleic acid has been used in the examples of the present invention but it should be understood that this is by way of non-limiting example only and that other unsaturated fatty acids may be used instead. In the context of the present application, where reference is made to an unsaturated fatty acid 20, it is to be understood that this is intended to refer to any organic compound comprising a carboxylic acid head group covalently bound to an aliphatic tail comprising in between 10-30 carbon atoms and at least one carbon-carbon double bond in the aliphatic tail. The aliphatic tail may terminate in a non-aromatic ring structure, e.g. a five-membered or 6-membered cyclopentyl or cyclohexyl group, which may itself contain at least one double bond. A non-limiting example of an organic compound intended to fall within the above definition of an unsaturated fatty acid 20 is retinoic acid. Many other compounds in addition to the example compounds explicitly mentioned in the present application will be immediately apparent to the skilled person.

The elastomer 10 and the unsaturated fatty acid 20 may be mixed in any suitable ratio in a composition to form the bulk-modified elastomer. Preferably, unsaturated fatty acid 20 is present in such a composition in a range of 0.05-35% by weight of the elastomer 10 such that upon bulk modification of the elastomer 10 the bulk-modified elastomer retains its flexibility to the remaining presence of carbon-carbon double bonds in the elastomer bulk.

An example synthesis procedure for producing the bulk-modified elastomer from a polyene such as polybutadiene is given below (synthesis example 1).

Synthesis Example 1

Polybutadiene chunks as obtained from Lanxess AG, Cologne, Germany are inserted into a compounder or mix extruder. The chunks contain a peroxide such as Dicumylperoxide as a catalyst. An amount of linoleic acid (60-74% concentrated as obtained from Aldrich Chemistry) in a range of 1-30 wt % by weight of the polybutadiene chunks is mixed into the polybutadiene bulk by kneading at a temperature in the range of 110-150° C. The resulting extruded mixture is injected into a stainless steel mold defining a fluidic device and having an oxidized inner surface contacting the extruded mixture for 3-10 minutes at a temperature in a range of 150-200° C. to yield a monolithic fluidic device module of a polybutadiene rubber cross-linked with the linoleic acid.

An example synthesis procedure for producing the bulk-modified elastomer from a silicone rubber is given below (synthesis example 2).

Synthesis Example 2

A 121 g sodium linoleate solution in water (30 wt %) is mixed into silicone component A (240 g) of Elastosil LR 3040 from Wacker Chemie AG and vigorously stirred under vacuum conditions at room temperature to evaporate the water from the composition. The resultant mixture is mixed with component B (277 g) of Elastosil LR 3040 from Wacker Chemie AG (including Pt-catalyst) and fed into an injection molding apparatus where the resultant mixture is injected into a stainless steel mold having an oxidized inner surface contacting the resultant mixture and defining a fluidic device module and molded for 10-60 seconds at a temperature in a range of 150-200° C. to yield a monolithic fluidic device module of a silicone rubber cross-linked with the sodium linoleate. At higher concentrations of sodium linoleate extra cross linker (polymethylhydrosiloxane) may be added to the reaction mixture to prevent an excess of double bonds of the unsaturated fatty acids decreasing the conversion rate. The molded product is subsequently dropped in an aqueous HCl solution (pH 2-4) to convert at least the sodium carbonate groups at the surface of the molded product into free carboxylic acid groups.

Figure 2:
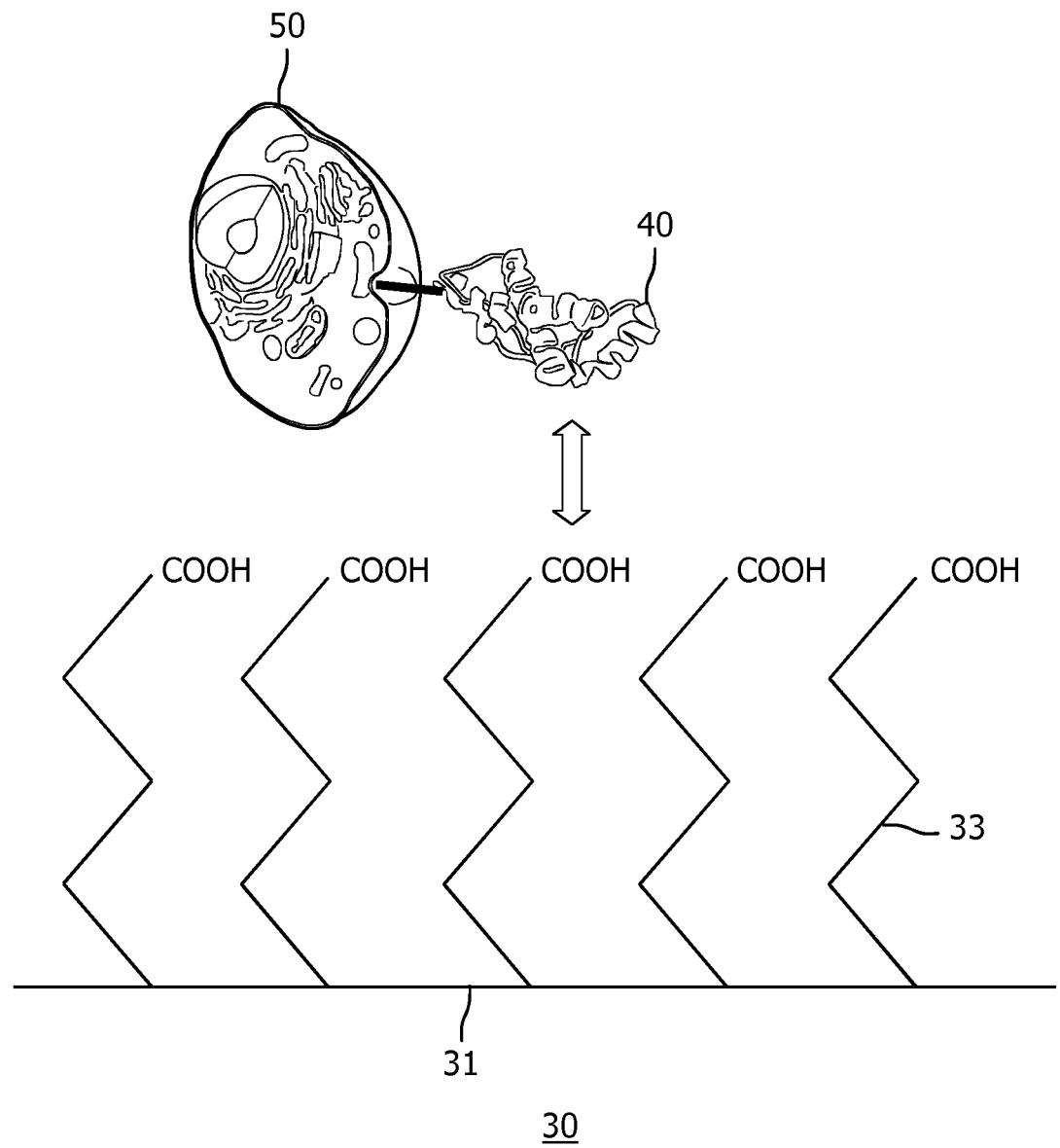
FIG. 2 schematically depicts the immobilization of mammalian cells on a cell scaffold including such a bulk-modified elastomer.

The thus bulk-modified elastomer may be made biocompatible by reacting the free carboxylic acid groups on its surface with a cell-culturing protein such as fibronectin, collagen or elastin. This is schematically depicted in FIG. 2 in which a cell-culturing protein 40 can be bound to the free carboxylic acid groups of the fatty acid tails 33 extending from a surface 31 of the bulk-modified elastomer 30 to form a cell culturing scaffold. The cell-culturing protein 40 of such a cell culturing scaffold can stabilize mammalian cells or tissue 50, e.g. human tissue, such that the cells 50 remain alive and multiply normally over a prolonged period of time, as the cell-culturing protein 40 mimics the natural environment of such cells, as is well-known per se. A well-documented binding protocol for covalently binding fibronectin to surface carboxylic acid groups is given below:

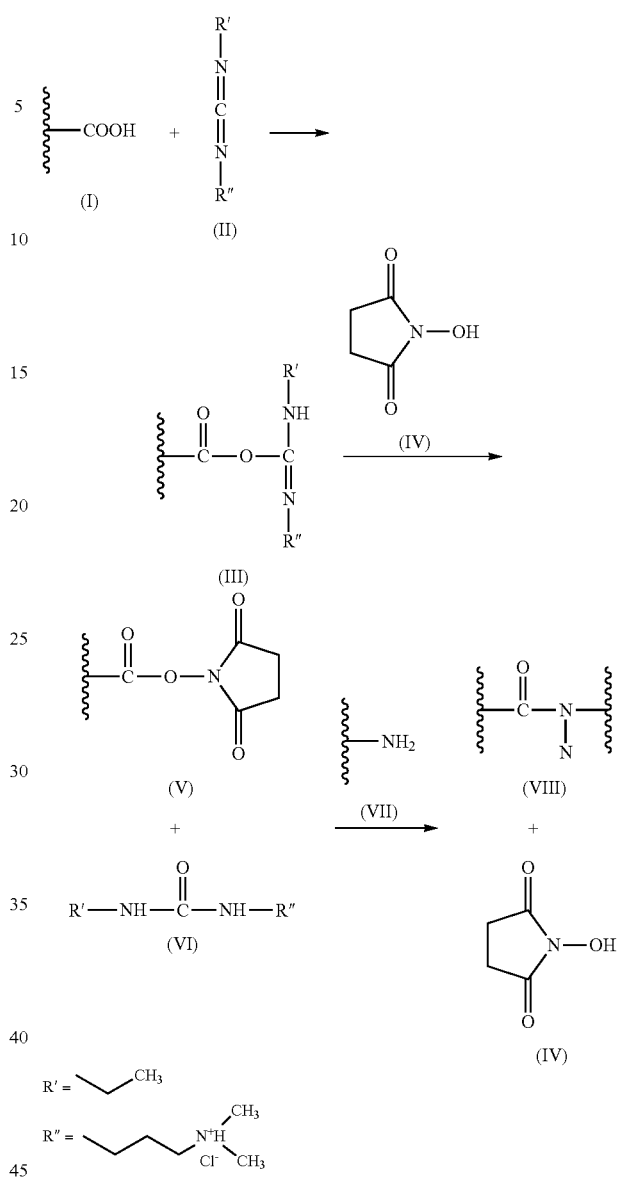

A description of this protocol can be found in: L. H. H. Olde Daminnk, P. J. Dijkstra, M. J. A. Luyn, P. B. v. Wachem, P. Nieuwenhuis, and J. Feijen, "Cross-linking of dermal sheep collagen using a water-soluble carbodiimide", Biomaterials, 17(8) pp. 765-774 (1996).

In this protocol, the carboxylic acid groups (compound I) may be reacted with 1-ethyl-3-(3-dimethylaminopropyl) carbodiimide hydrochloride (EDC, compound II) followed by a reaction with N-hydroxysuccinimide (NHS, compound IV), which can react with the amine groups of fibronectin (compound VII) to covalently bind the fibronectin to the carboxylic acid groups of the bulk-modified elastomer 30. In this manner, the fibronectin can form a scaffold for carrying and culturing mammalian cells. As is well-known per se, the integrin receptors of such cells can recognize specific amino acid sequences of the fibronectin, e.g. a sequence such as an Arg-Gly-Asp-Ser sequence, which triggers the cells to accept the new environment and stay alive. As previously explained, such a scaffold can be formed with high uniformity in terms of coverage of the surface of the bulk-modified elastomer 30, e.g. the surface of a membrane of a fluidic device module due to the high density homogeneous distribution of the carboxylic acid groups across such a surface.

Figure 3:
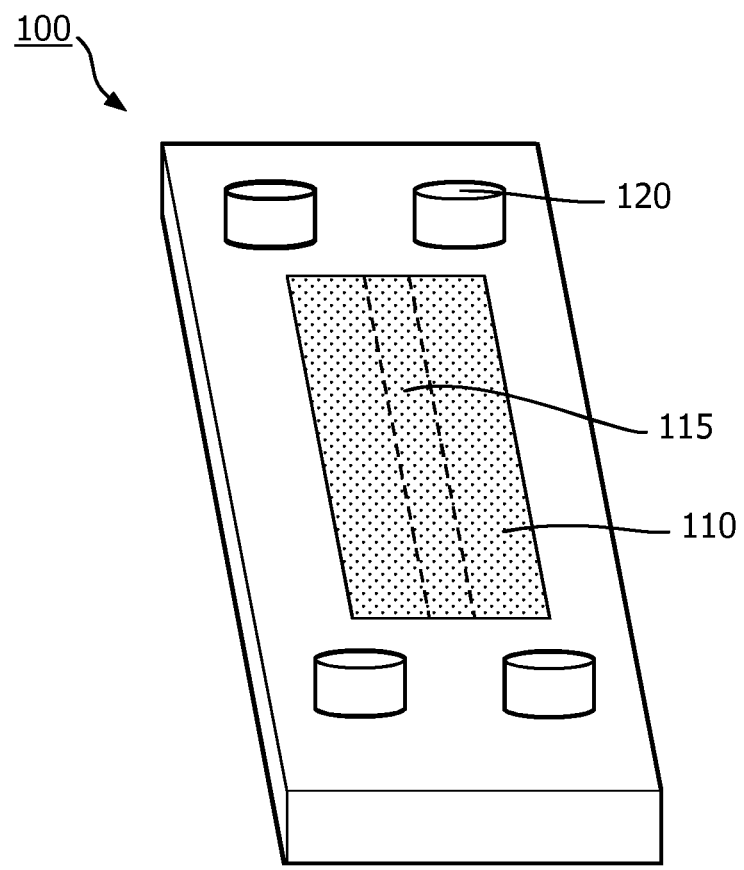
FIG. 3 schematically depicts a perspective view of a fluidic device module according to an embodiment.
Figure 4:
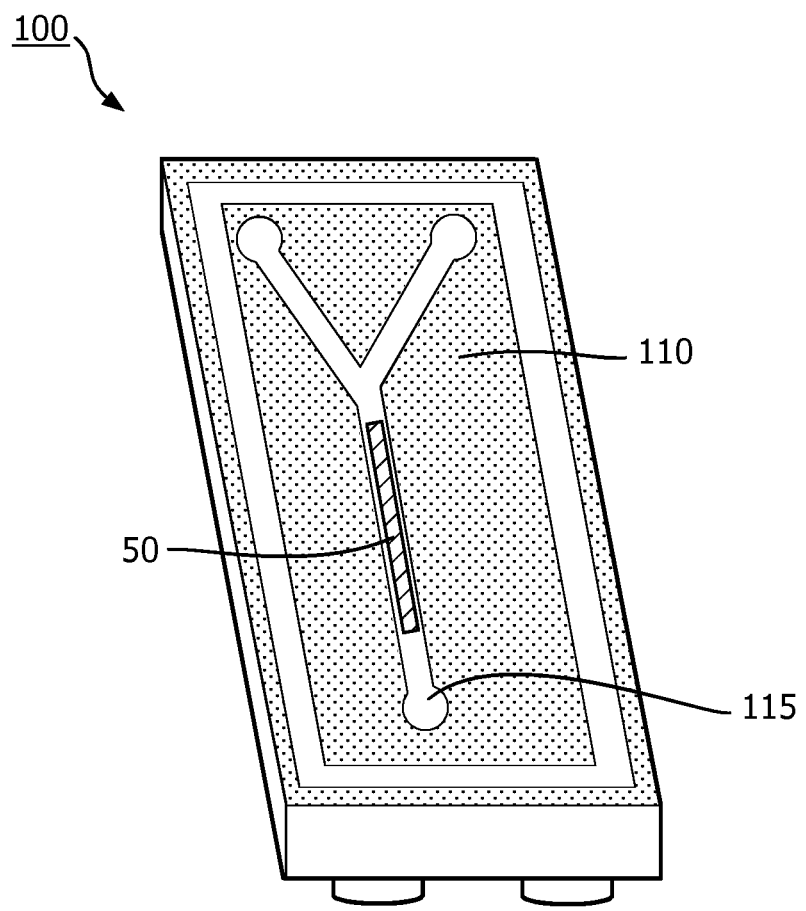
FIG. 4 schematically depicts another perspective view of a fluidic device module according to an embodiment.

A typical example of a fluidic device module 100 is schematically depicted in FIG. 3 and FIG. 4, in which perspective views of opposing major surfaces of the fluidic device module 100 are schematically depicted. The fluidic device module 100 may comprise a membrane 110 over which at least one flow channel 115 extends. Preferably, the fluidic device module 100 comprises opposing flow channels spatially separated by the membrane 110. At least the membrane 110 is made of the bulk-modified elastomer 30 although in a preferred embodiment the entire fluidic device module 100 is made of the bulk-modified elastomer 30, thereby yielding a monolithic fluidic device module 100.

The fluidic device module 100 may comprise one or more septums 120 through which such flow channels 115 may be accessed. Each flow channel 115 preferably is accessible through a dedicated set of septums 120, such that cross-contamination between multiple flow channels 115 is avoided. As explained above, the fluidic device module 100 may be made bio-compatible by reacting the carboxylic acid groups on the membrane 110 as explained above to covalently bind a cell culturing protein, e.g. fibronectin, collagen or elastin, to the membrane 110, such that cells 50 may be cultured on the thus formed cell culturing scaffold of the biocompatible membrane 110. As such cell immobilization procedures on biocompatible membranes including such cell-culturing proteins are well-known per se, this will not be explained in further detail for the sake of brevity only. It suffices to say that any suitable protocol may be used for this purpose.

The membrane 110 may comprise a plurality of holes or grooves such that liquid nutrition and solutions with compounds such as potential drugs may reach both sides of the membrane and cells/tissue, which holes or grooves may be formed in any suitable manner, e.g. through laser cutting. Because the membrane 110 can be made biocompatible as explained above, the size and pitch of these holes or grooves is less critical than in prior art devices in which the holes or grooves used to immobilize and culture cellular material. In other words, such holes or grooves in the membrane 110 of the fluidic device module 100 may be substantially larger than a typical diameter of the cells to be immobilized on the membrane 110, with the pitch between such holes or grooves not being particularly critical.

Figure 5:
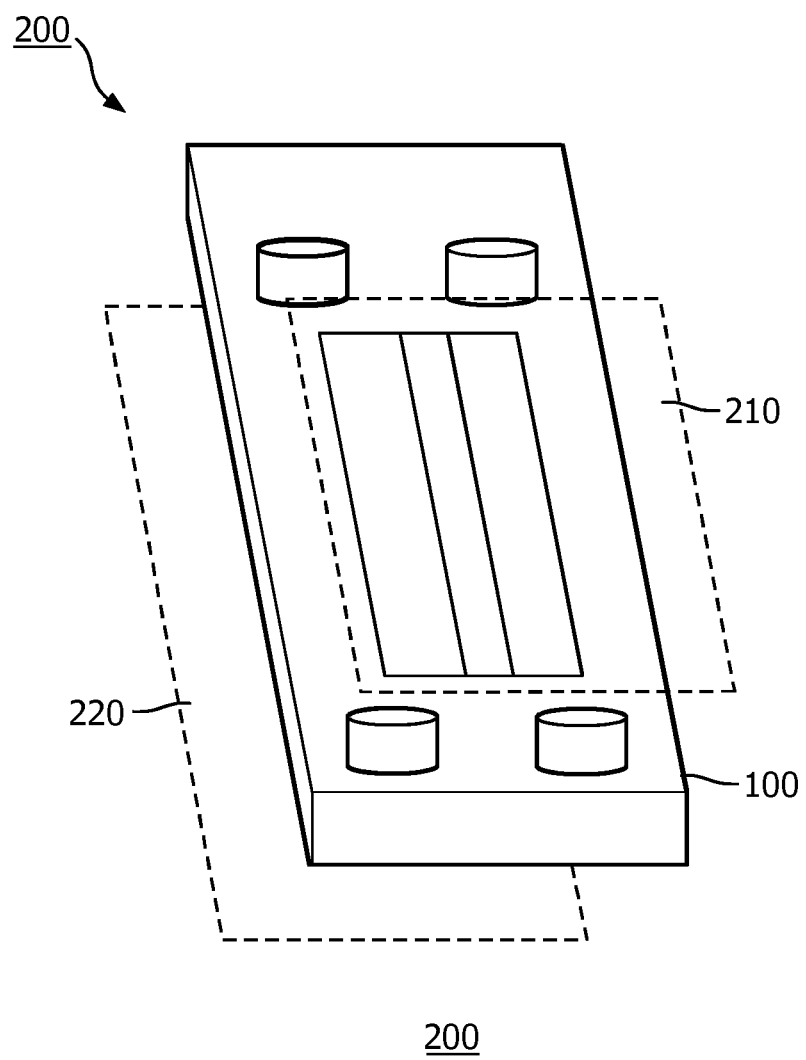
FIG. 5 schematically depicts an exploded view of a fluidic device according to an embodiment.

A fluidic device 200 as schematically depicted in FIG. 5 may be formed from such a fluidic device module 100 by the provision of a pair of cover plates 210, 220, which cover plates fluidly seal the fluidic device module 100 such that fluids passed through the one or more flow channels 115 of the fluidic device module 100 cannot leak out of the fluidic device 200.

In an embodiment, the cover plates 210, 220 are arranged such that the cover plate 210 covers a first major surface of the fluidic device module 100, thereby sealing a first fluidic channel 115 of the fluidic device module and the other cover plate 220 covers a second major surface of the fluidic device module 100, thereby sealing a second fluidic channel 115 of the fluidic device module. The cover plates 210 and 220 may be made of any suitable material, e.g. glass or a plastic material. Preferably, the cover plates are stretchable and flexible to ensure a good fit with the fluidic device module 100 whilst retaining the flexibility of the fluidic device module 100 in the fluidic device 200. Such a fluidic device 200 may be deployed as an organ on chip as will be readily understood by the skilled person.

Figure 6:
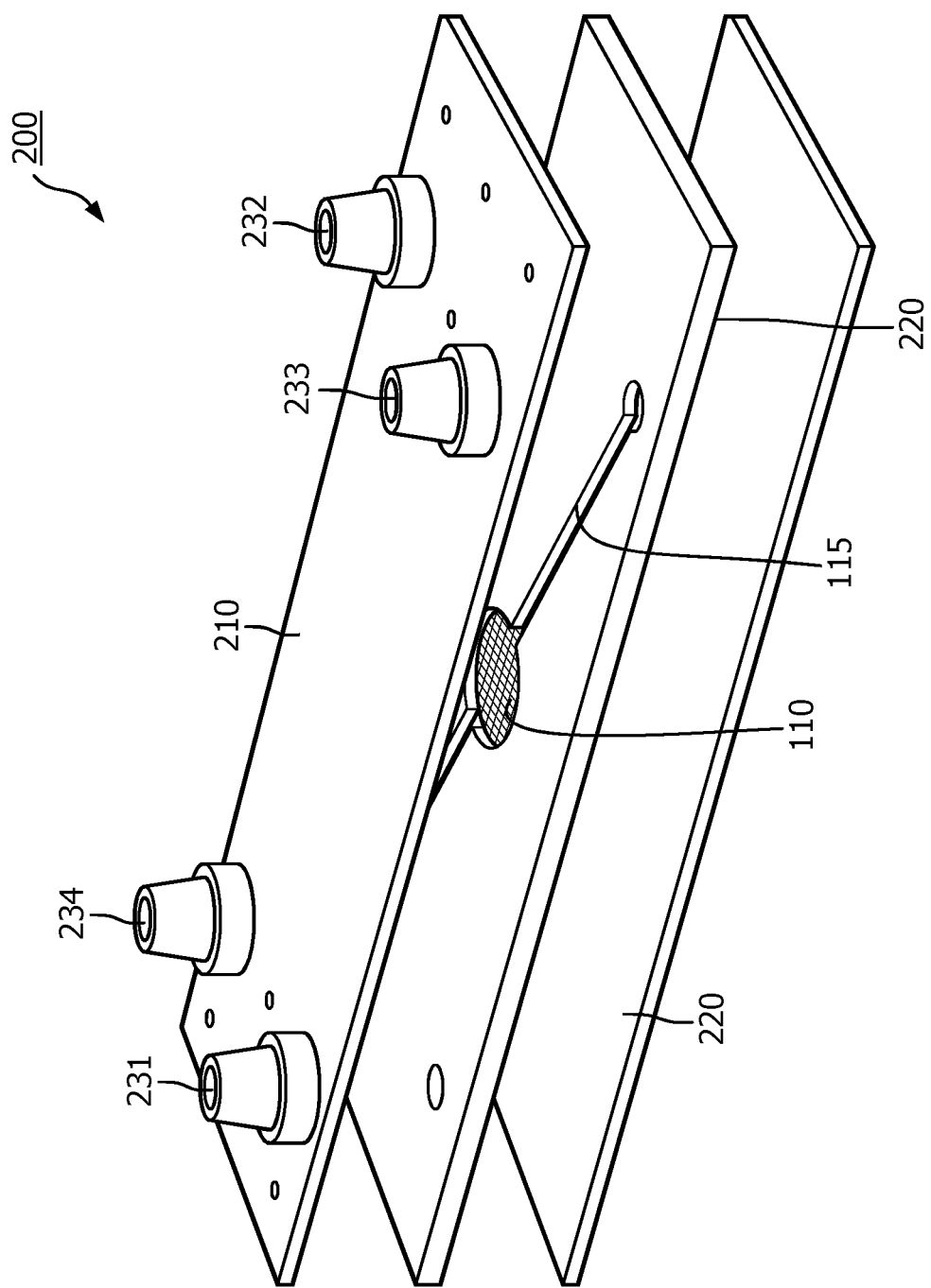
FIG. 6 schematically depicts a perspective view of a fluidic device according to another embodiment.

FIG. 6 schematically depicts an example embodiment of a fluidic device 200 in which the device comprises a fluidic device module 100 according to the present invention in between two rigid cover plates 210 and 220. The upper plate 210 comprises a first inlet 231 and a first outlet 232 in fluid connection with a lower channel (not visible) underneath the membrane 110 in the fluidic device module 100 such that the membrane 110 is in fluid contact with a fluid passing through this lower channel. The upper plate 210 further comprises a second inlet 233 and a second outlet 234 in fluid connection with an upper channel 115 over the membrane 110 such that the membrane 110 is in fluid contact with a further fluid passing through this upper channel 115. For example, the fluid passing through the lower channel may comprise drugs to be tested on the cell cultures attached to the membrane 110 as explained in more detail below, which can reach the cell cultures through the membrane 110 owing to the fact that the membrane 110 is made porous, e.g. by laser drilling holes or grooves in the membrane 110 as previously explained. Alternatively, such holes or grooves may be formed in the membrane 110 when forming the fluidic device module 100 in the polar mold. This has the advantage that a regular pattern of such fluid passages (pores) may be formed through the membrane 110. The further fluid passing through the upper channel 115 may be in direct contact with such cell cultures and provide such cell cultures with nutrients. The inlets 231, 233 and the outlets 232, 234 in some embodiments are septa through which fluids may be hydraulically pumped over the membrane 110 through the aforementioned channels, e.g. by pressing the septa. Alternatively, the inlets 231, 233 and the outlets 232, 234 may be ferrules to which tubing may be attached, e.g. clamped, which for instance is useful when the fluidic device 200 is used as a well plate or the like in a lab on chip system.

Figure 7:
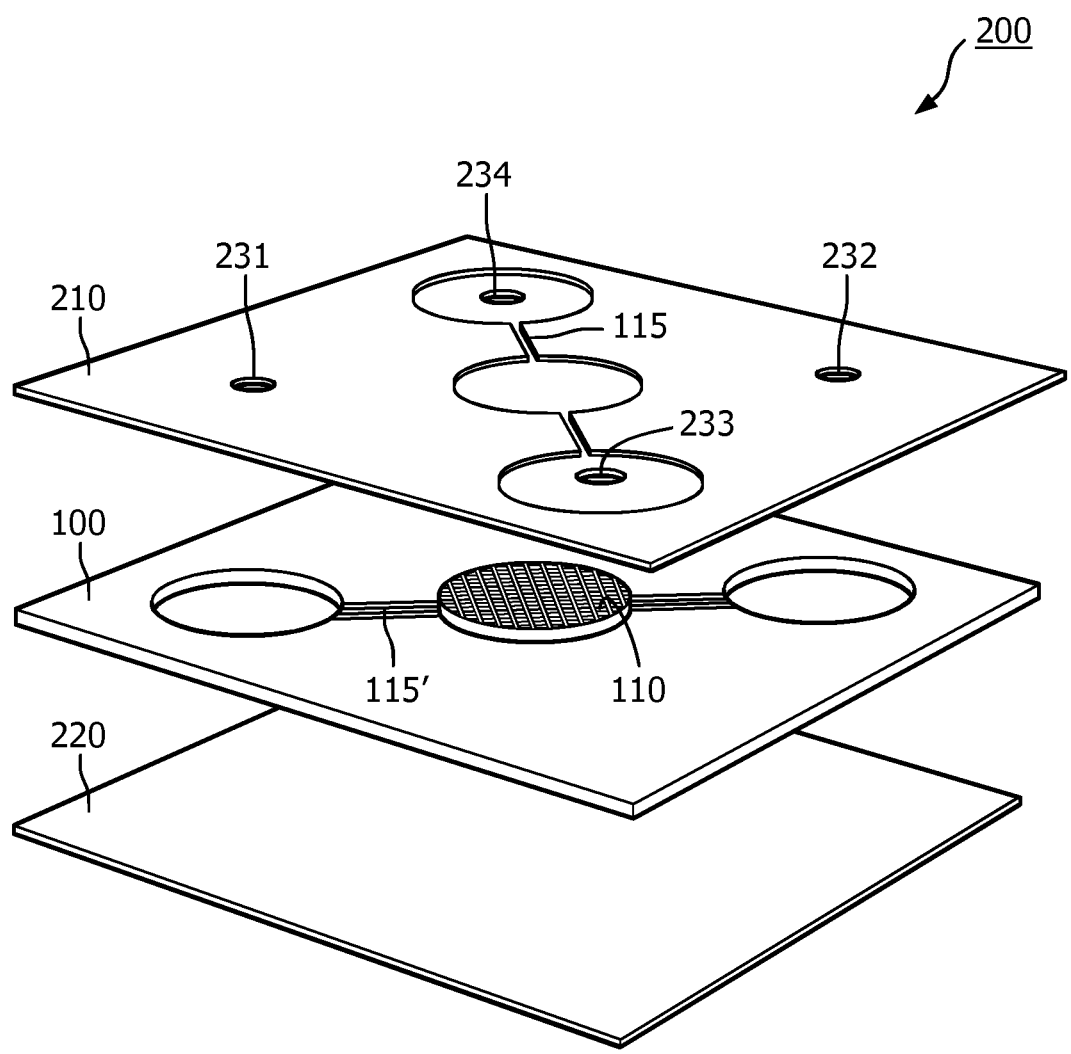
FIG. 7 schematically depicts an exploded perspective view of a fluidic device according to yet another embodiment.
Figure 8:
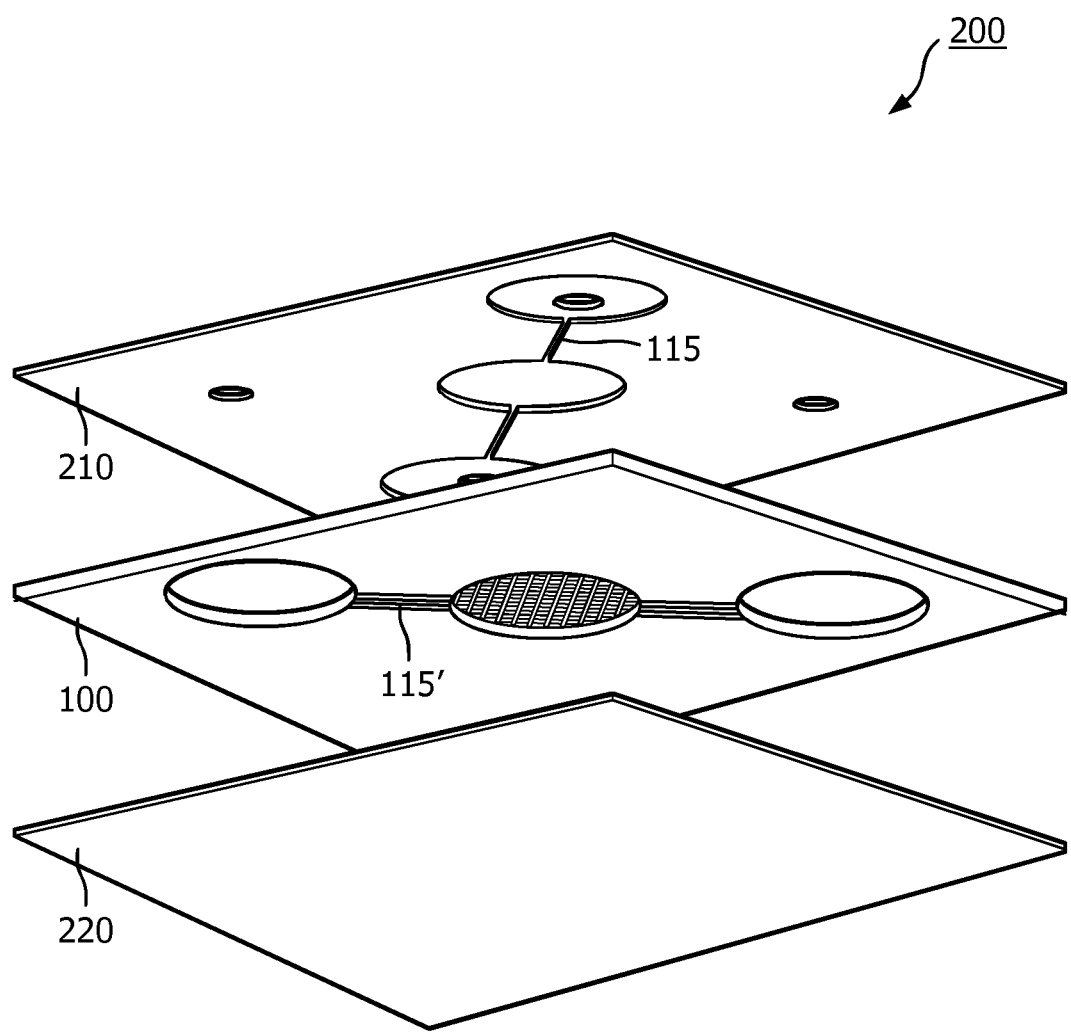
FIG. 8 schematically depicts another exploded perspective view of the fluidic device of FIG. 7.

In an embodiment, the upper and lower channels are incorporated in the (monolithic) fluidic device module 100, e.g. when molding the fluidic device module 100. Alternatively, at least one of the upper and lower channels may be formed in one of the cover plates. FIG. 7 schematically depicts a perspective top view and FIG. 8 schematically depicts a perspective bottom view of an example embodiment of a fluidic device 200 in which the upper channel 115 is formed in the upper cover plate 210 whilst the lower channel 115' is formed in the fluidic device module 100. It is of course equally feasible to form the lower channel 115' in the bottom cover plate 220 as will be readily understood by the skilled person. The fluidic device 200 such as the device shown in FIG. 7 and FIG. 8 for example may be used as a microwell in a lab on chip device in which a plurality of such microwells may be clamped or otherwise secured to facilitate parallel testing of a plurality of different samples within a single lab on chip device, in which each microwell typically comprises one of these samples.

Upon immobilizing a cell culture 50 in such a fluidic device 200, typically after the membrane 110 has been made biocompatible as explained above, the fluidic device 200 may be used in methods in which the immobilized cell culture 50 is exposed to a fluid comprising a compound of interest, which fluid may be passed through a flow channel 115 of the fluidic device 200 in order to expose the immobilized cell culture 50 to the compound of interest in the fluid and monitor the reaction of the immobilized cell culture 50 to such exposure. Such a method for example may be deployed in an oncology setting where the immobilized cell culture 50 may be exposed to a drug, e.g. a chemotherapy drug, in order to monitor the response of the immobilized cell culture 50 to such a drug. To this end, the immobilized cell culture 50 may include tumor cells in order to test the efficacy of the drug and/or may include healthy cells in order to test the toxicity of the drug on healthy tissue.

Such a drug testing method typically involves providing a fluidic device module 100 in accordance with one or more embodiments of the present invention, e.g. providing a monolithic fluidic device module 100 and binding at least the membrane 110 of the fluidic device module 100 to a cell culturing protein 40, e.g. fibronectin, to obtain a cell culturing scaffold. Next, a harvested cell culture 50 is applied to the cell culturing scaffold to obtain a prepared fluidic device module 100 from which a fluidic device 200, e.g. an organ on chip, is formed as previously explained. The cell culture within the fluid device 200 may be fed through one of a pair of flow channels 115 of the fluidic device 200 in order to keep the cell culture alive, whilst the cell culture may be exposed to a drug to be tested through the other of the pair of flow channels 115 of the fluidic device 200, with the drug testing method typically being completed by monitoring the response of the cell culture 50 to the drug to be tested. This for example may be achieved by disassembling the fluidic device 200 by removing the cover plates 210, 220 and slicing the fluid device module 100 such that a slice of this module including a portion of the cell culture 50 is obtained, which slice may be investigated under a microscope or the like in order to investigate the effects of the drug under test on the cell culture 50. During such investigations, the cell culture 50 is typically stained, treated with formalin and fixated in a fixating agent such as paraffin to facilitate such microscopic investigation. Such staining, treating and fixating of the cell culture 50 may be deployed within the fluidic device 200, e.g. by passing the appropriate chemical agents through a fluidic channel 115 of the fluidic device 200 in which the cell culture 50 is exposed.

In an alternative embodiment, such disassembly of the fluidic device 200 can be avoided and the monitoring of the response of the cell culture 50 to one or more compounds such as a drug to be tested can be achieved in real time using confocal microscopy. In particular, where embodiments of the fluidic device 200 comprise transparent cover plates 210, 220, e.g. glass plates or polymer plates, confocal microscopy may be used to monitor the cell culture 50 within an assembled fluidic device 200. This is made possible through the fact that at least the bottom cover plate 220 can be kept thin, for example having a thickness in a range of 150-300 µm, with the distance between the membrane 110 of the fluidic device module 100 carrying the cell culture 50 and the bottom cover plate 220 being less than 200 µm such that the focal length limits of confocal microscopy (typically around 500 µm from the object to be investigated to the lens objective). To this end, the membrane 110 may have a thickness in a range of 10-100 µm, such as a thickness of 20-30 µm. The thickness of the upper cover plate 210 is not critical; any suitable thickness may be contemplated, such as a thickness of 300 µm-3 mm.

The evaluation of the cell culture 50 within the fluidic device 200 using confocal microscopy is particularly suitable where the cell spheroids have a diameter of less than 500 µm, e.g. about 200 µm in order to ensure that the overall focal length of the optical path facilitates the capture of a sharp image with the confocal microscope. For larger spheroids, the fluidic device 200 may have to be dismantled such that the membrane 110 including the spheroids can be pressed onto a glass cover slip for positioning in the optical objective of the confocal microscope.

It is furthermore noted that the aforementioned dimensions of the fluidic device 200 typically apply during the real-time monitoring of the cell culture 50 within the fluidic device 200. In embodiments in which the fluidic device 200 is sliced as previously explained, e.g. for digital pathology, the dimensions of the fluidic device 200 are less critical as long as the formalin and paraffin fixation can be performed thereon.

As will be readily understood by the skilled person, such drug testing methods may significantly differ in terms of protocol, e.g. drug dosages, administration frequencies, and so on. It should be understood that the drug testing method of the present invention is not limited to a particular protocol as long as such methods may be deployed using a fluidic device 200 according to an embodiment of the present invention in which at least the membrane 110 is made biocompatible by converting it into a cell culturing scaffold by reacting its carboxylic acid groups with a cell culturing protein as previously explained.

At this point, supplementary evidence is provided for the cross-linking reaction between the elastomer 10 and the carbon-carbon double bonds of the unsaturated fatty acid 20, as well as for the successful binding of fibronectin to (the carboxylic acid groups of) such a bulk-modified elastomer.

In the following, FT-IR spectra were recorded using a Thermo iS50 FTIR bench in combination with a heatable Golden Gate ATR module. An average of 64 scans was used for all measurements. In the measurements, the resolution was set to 4 cm$^{-1}$ using a spectral range from 4000-650 cm$^{-1}$. To allow for such a resolution to be used, the internal spectrometer aperture was set to 50%.

Raman spectra were recorded using a Renishaw InVia Raman microscope combined with a laser excitation wavelength of 514 nm provided by a Coherent Innova 70C Ar$^+$ laser. A 50 mW excitation power was used in combination with a 63× glass correction objective. The spectra were recorded through a glass top cover using a grating consisting of 1200 lines/mm and with a 2 s integration time over a spectral range of 662-3,000 cm$^{-1}$ using an average of 300 spectra such that each spectrum took 600 s to be recorded.

Figure 9:
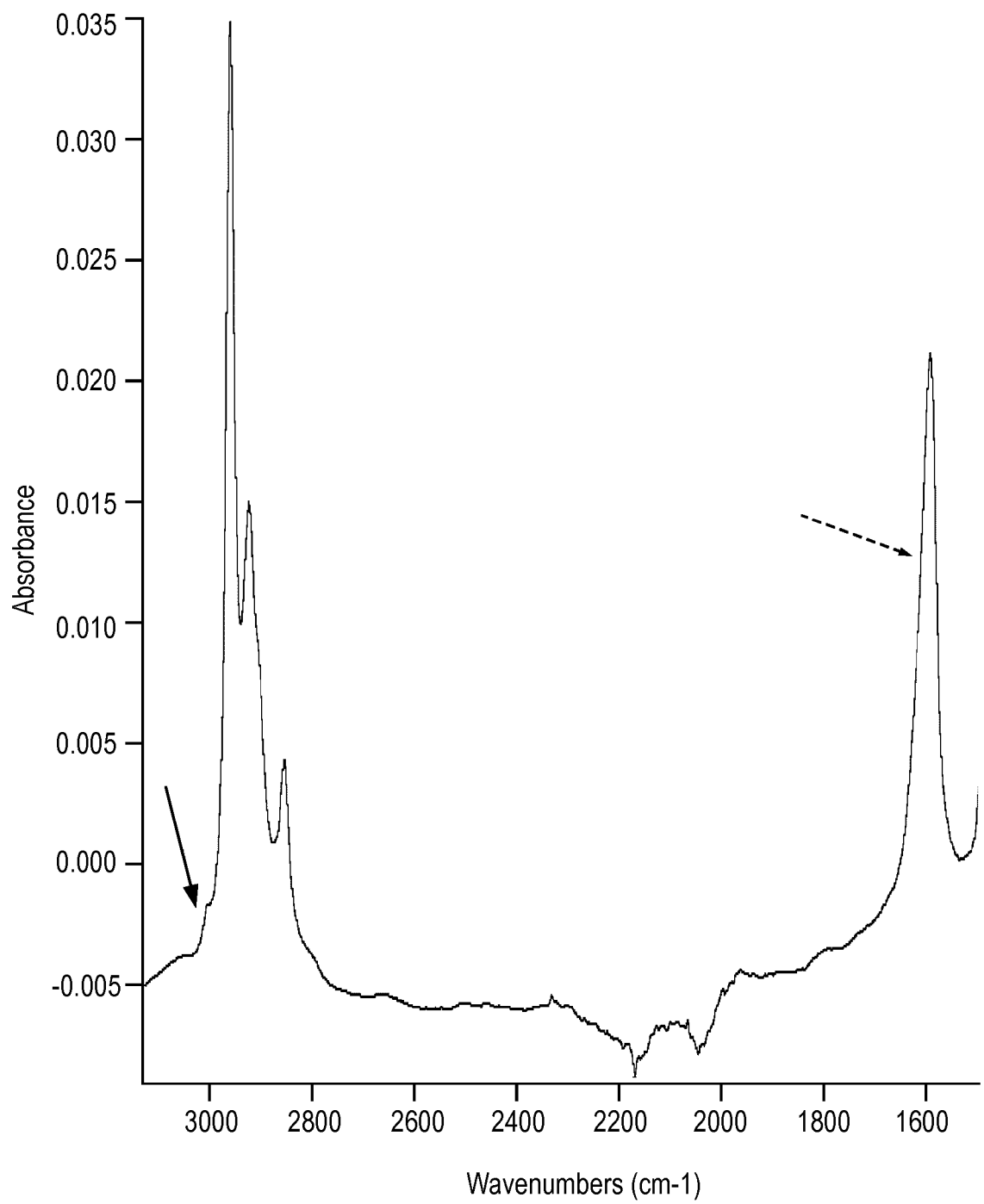
FIG. 9 is part of an FT-IR spectrum of a composition for forming a bulk-modified elastomer according to an embodiment.
Figure 10:
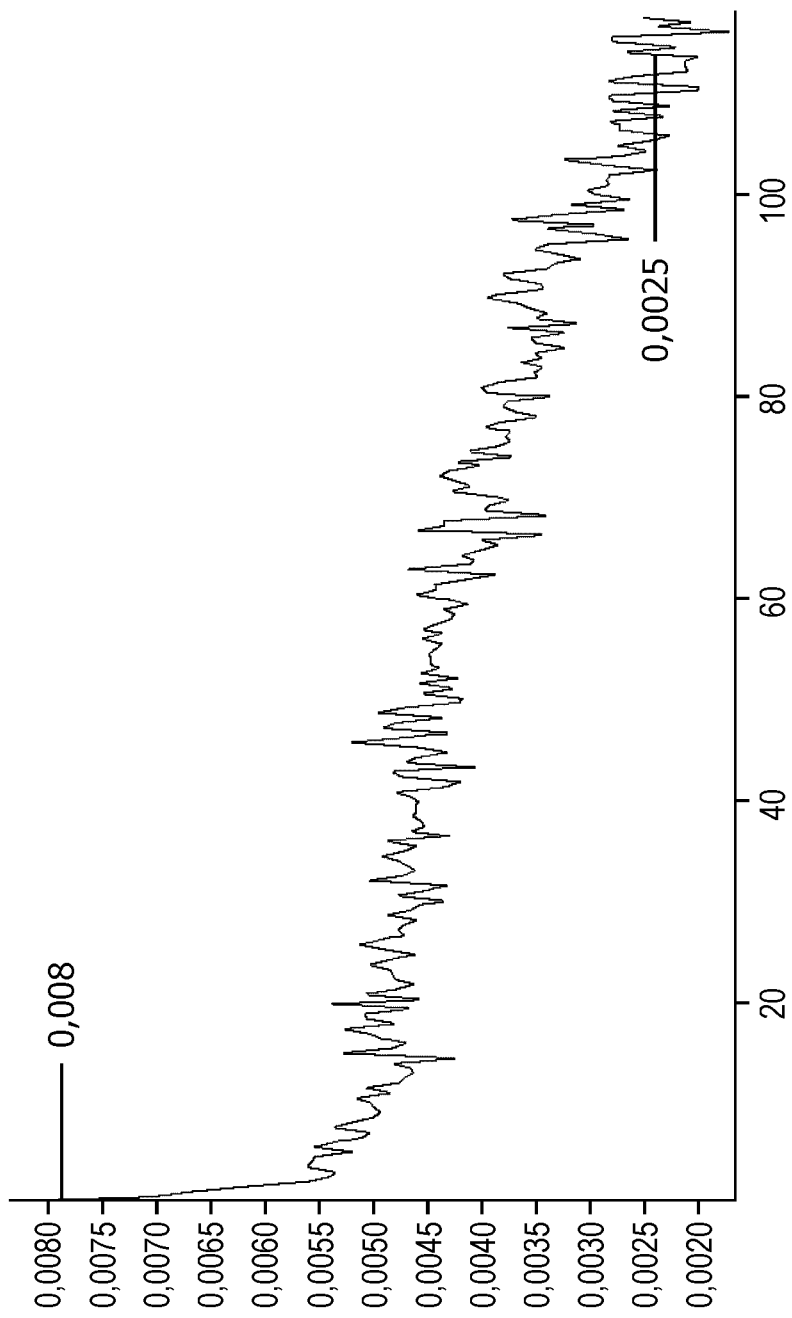
FIG. 10 depicts a change in ratio between the intensity of two characteristic peaks in the FT-IR spectrum of FIG. 9 as a function of the bulk modification reaction time.

FIG. 9 depicts part of an FT-IR spectrum of sodium linoleate. The solid arrow indicates a C—H stretch vibration at approximately 3,050 cm$^{-1}$, which has been assigned to the C—C double bonds of the sodium linoleate, whereas the dashed arrow indicates the C═O stretch vibration at approximately 1600 cm$^{-1}$, which has been assigned to the carboxylate groups of the sodium linoleate. FIG. 10 depicts a ratio between the intensity of this C—H stretch vibration and C═O stretch vibration as a function of time during monitoring of the progress of a reaction according to aforementioned synthesis example 2. The samples were recorded in between two quartz plates whilst heating the samples to 200° C. to induce the cross-linking reaction. As can be clearly seen from FIG. 10, a reduction in C—C double bonds in the sodium linoleate can be seen during the cross-linking reaction whilst the carboxylate stretch vibration intensity remains unaltered, which provides a clear indication that the C—C double bonds are being consumed in the cross-linking reaction, thereby clearly suggesting cross-linking between the sodium linoleate and the silicone elastomer.

Figure 11:
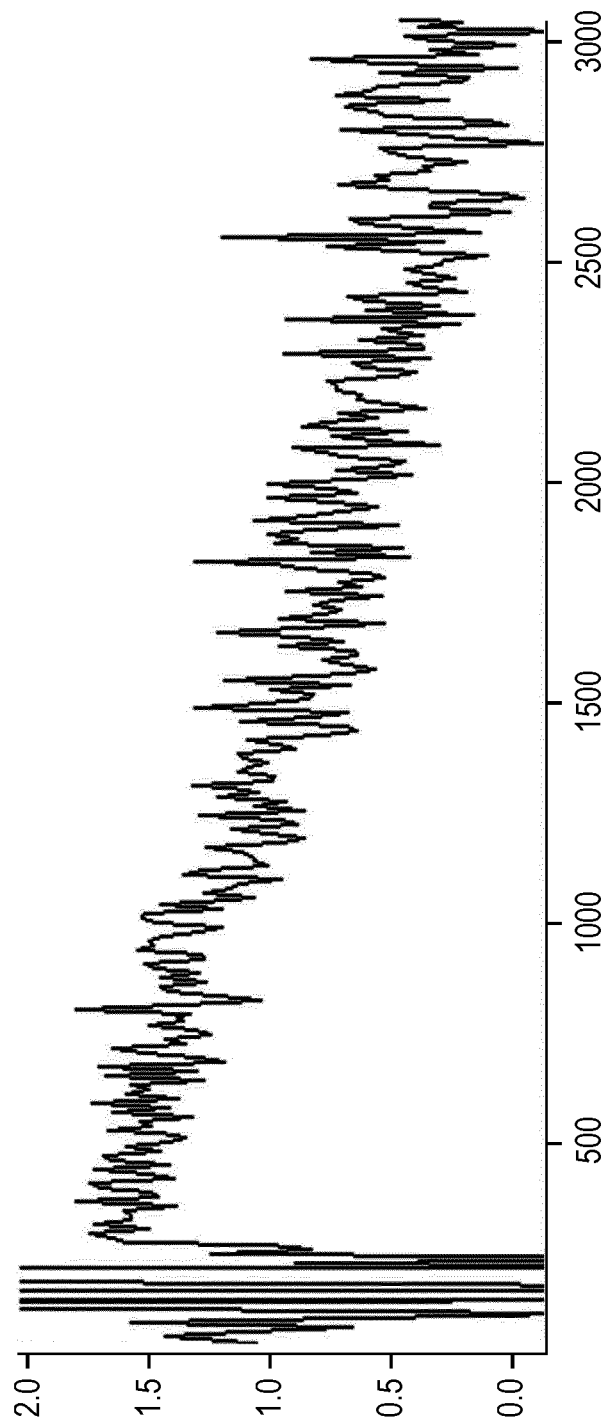
FIG. 11 depicts a Raman spectrum of the $C=C$ stretch vibration of the unsaturated fatty acid as a function of the bulk modification reaction time.

To further corroborate this, the cross-linking reaction was further monitored with Raman spectroscopy, using the same sample setup as used for the recordal of the FT-IR spectra in order to minimize the impact of environmental oxygen on the crosslinking reaction. In the Raman spectrum, the C═O stretch vibration was inactive whilst the C═C stretch vibration showed clear activity as depicted in FIG. 11.

Upon initial thermal stabilization of the sample up to t=250 s (during which the sample is thermally equilibrated with the laser used in the Raman spectroscopy), the Raman spectrum shows a steady decrease in the C=C stretch vibration of the sodium linoleate, thereby clearly indicating that these bonds are active in the cross-linking with the silicone elastomer.

Figure 12:
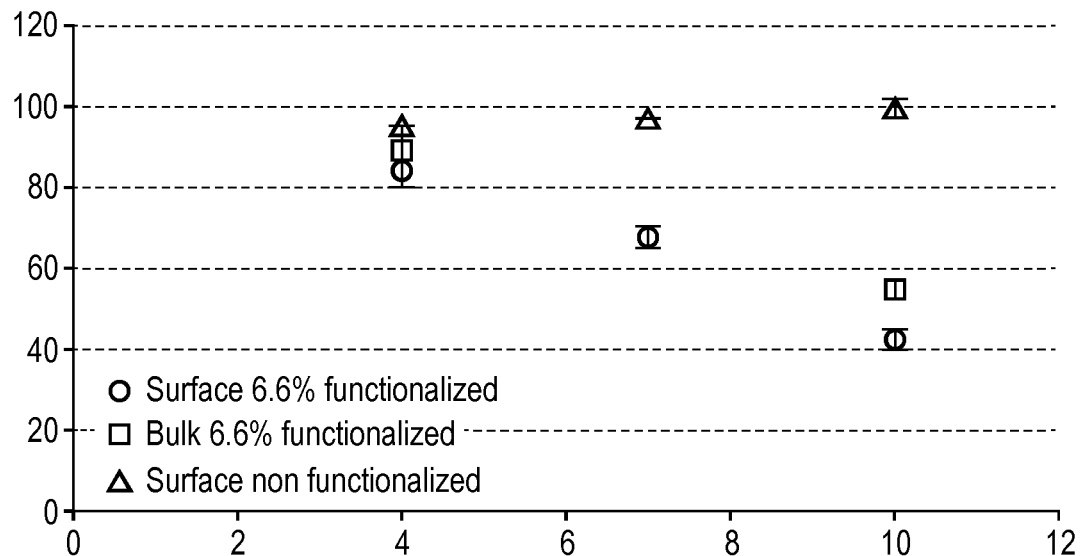
FIG. 12 is a graph of contact angle measurements of a modified and a non-modified silicone-based elastomer.
Figure 13:
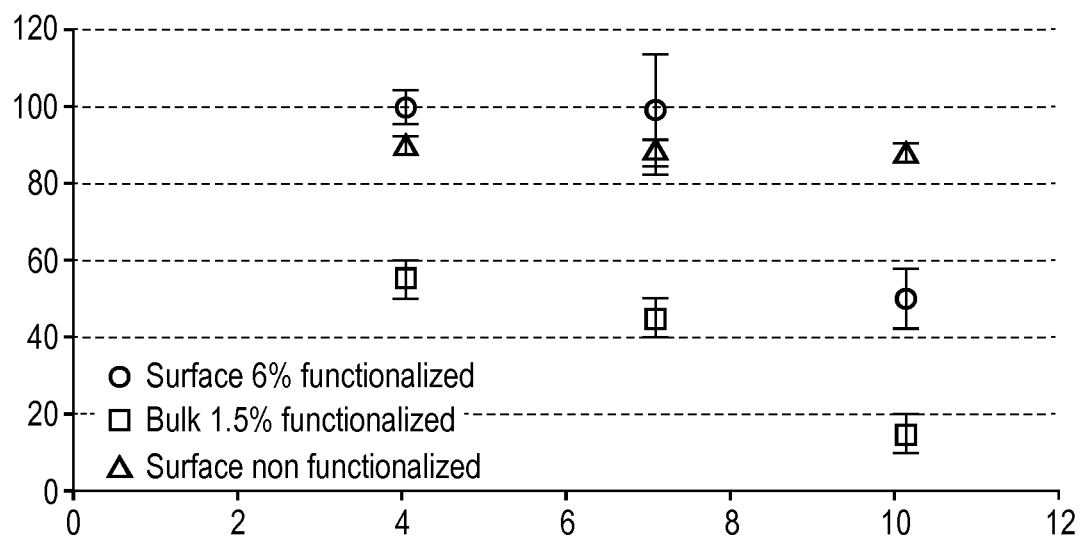
FIG. 13 is a graph of contact angle measurements of a modified and a non-modified polybutadiene-based elastomer.

To further demonstrate the bulk modification of the elastomers in synthesis examples 1 and 2, a block of each elastomer after reaction with the linoleic acid was molded in a polar mold as previously explained and subsequently sliced with a microtome at −40° C. to obtain an internal slice of the modified elastomer, i.e. a slice in which none of its major surfaces were external surfaces of the molded elastomer block. These internal slices were subsequently brought into contact with a 2 µl droplet of water of different pH (pH 4, pH 7 and pH 10) for 3 minutes after which the contact angles of the water droplets with these internal slices were measured. The same procedure was repeated with unmodified elastomers to compare the measured contact angles of an internal slice of the linoleic acid modified elastomers against the measured contact angles of an internal slice of the corresponding unmodified elastomer. The results for the silicone-based elastomer are shown in the graph in FIG. 12 and the results for the polybutadiene-based elastomer are shown in the graph in FIG. 13. For the silicone-based elastomer, a functionalized elastomer formed using 6.6 wt % linoleic acid was used for both the bulk and surface contact angle measurements, whereas for the polybutadiene elastomer a functionalized elastomer formed using 6 wt % linoleic acid was used for the surface contact angle measurements and a functionalized elastomer formed using 1.5 wt % linoleic acid was used for the bulk contact angle measurements. This difference in concentration of the linoleic acid between surface and bulk contact angle measurements for the polybutadiene elastomer merely is the result of availability of samples at the time of measurement.

As can be seen from these graphs, the internal slices of the polybutadiene crosslinked with linoleic acid and the silicone crosslinked with (saponified) linoleic acid both showed a strong pH dependency of the measured contact angle with decreasing contact angles being measured with increasing pH, whereas the measured contact angles of the unmodified polybutadiene and silicone were largely pH independent. Without wishing to be bound by theory, the small increase in contact angle measured for the unfunctionalized silicone with increasing pH may be result of a pH dependence on the hydrogen bonding between the water molecules and silanol moieties in the silicone.

The strong pH dependency of the measured contact angle for the bulk of the functionalized elastomers clearly demonstrates the presence of carboxylic acid groups within the bulk of the elastomers crosslinked with an unsaturated fatty acid such as linoleic acid. This can be understood as follows. At lower pH, such carboxylic acid groups remain largely protonated, thereby minimizing the surface charge of the internal slices of the elastomers. With increasing pH, this surface charge increases due to increased deprotonation of the carboxylic acid groups, which decreases the contact angle of the water droplets with the surface of these internal slices. On the other hand, where such carboxylic groups are not present at the surface exposed to the water droplets, such as in the unmodified elastomers, the change in pH of the water droplets does not cause a change in the surface charge, such that the measured contact angle of the water droplets of different pH with such a surface is far less sensitive to these pH changes.

To further demonstrate the ability of the material of the present invention to bind a cell culturing protein such as fibronectin, example embodiments of the material were bound to fibronectin, and surface plasmon resonance (SPR) spectra were recorded to demonstrate this binding reaction.

SPR experiments were performed on amine SPR chips (High capacity amine chip SPR affinity Sensors, Sierra Sensors, Hamburg, Germany) and on bare gold SPR chips (Bare gold 12 pk. SPR affinity Sensors, Sierra Sensors, Hamburg, Germany) spin coated with a solution of polybutadiene chunks and linoleic acid in n-heptane using a SPR2 spectrometer as provided by Sierra Sensors, Hamburg, Germany. The solution was prepared by dissolving the polybutadiene chunks in n-heptane in a glass bottle at 70° C. over a period of 72 hours whilst shaking the bottle, after which the linoleic acid was added and stirred into the mixture. After flow was observed and system was stabilized by flushing and degassing, an angle scan was performed to check the correlation between all channels. The angle scan data was saved and preceded with the essay for fibronectin cross-linking.

The chip surface was pre-conditioned by injecting 3 phases of 2 solutions over the surface. The first injection consisted of 60 µl of 100 mM Hydrochloric acid (HCl) at a flow rate of 10 µl/min and a dissociation time set to 1 second. The second injection consisted of 60 µl Elution buffer consisting of 1 M sodium chloride (NaCl) and 100 mM sodium hydroxide (NaOH) at a flow rate of 10 µl/min and dissociation time set to 1 second. The first phase consisted of injecting the solutions over channels 1 and 2, the second phase consisted of injecting the solutions over channels 3 and 4, whilst the third and final phase consisted of injecting the solutions over channels 1-4.

After the pre-conditioning all channels were cleaned and activated with EDC/NHS. This was done by mixing 100 µl EDC (1-ethyl-3-(3-dimethylaminopropyl) carbodiimide hydrochloride, Sigma-Aldrich, Saint Louis, USA) and 100 µl NHS (N-hydroxysuccinimide, Sigma-Aldrich, Saint Louis, USA) of 9.6 mg/ml in MilliQ stocks together, after which 60 µl of the mixture was injected onto the surface on all four channels at a flow rate of 10 µl min with a 1 s dissociation.

After all channels were pre-conditioned and activated with EDC/NHS, the channels were injected with 60 µl Fibronectin from bovine plasma powder (Bio Reagent, suitable for cell culture Sigma Aldrich, Saint Louis, MO, USA) dissolved in a sodium acetate buffer with pH 5.5 (Biacore, Diegem, Belgium) at a flow rate of 10 µl/min. Channel 2 was injected with 1 µg/ml Fibronectin with a dissociation time of 1 s, channel 3 was injected with 5 µg/ml Fibronectin with a dissociation time of is and channel 4 was injected with 10 µg/ml Fibronectin with a dissociation time of 1 s (channel 1 was used as a reference).

All four channels of the system subsequently were flushed with 60 µl running buffer PBS 0.05% Tween at a flow rate of 10 µl/min and a dissociation time of is to determine, whether fibronectin had truly bonded to the material of the present invention. Spectral data was saved and analyzed with analyzer program (Analyzer R2 Sierra Sensors Sierra Sensors, Hamburg, Germany).

Figure 14:
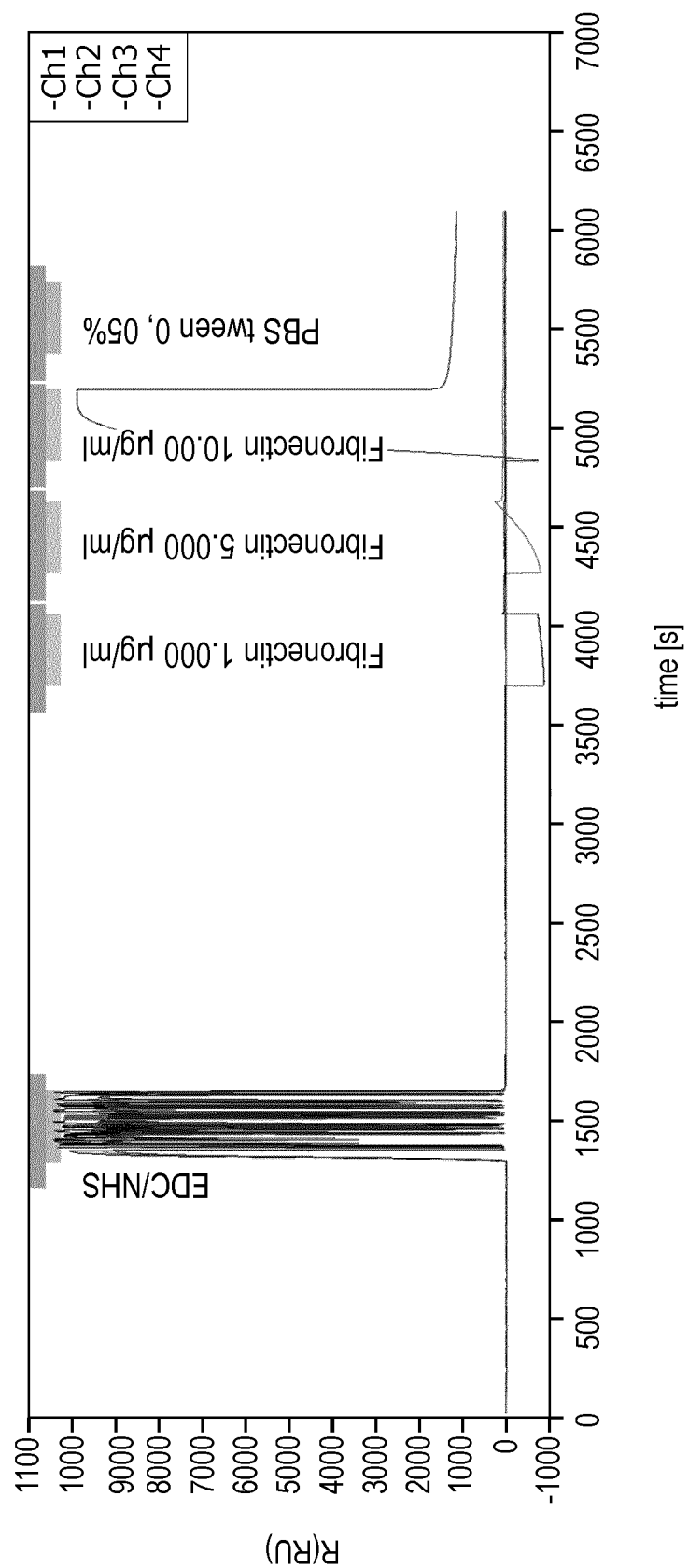
FIG. 14 and FIG. 15 depict surface plasmon resonance (SPR) spectra of a binding reaction between a bulk-modified elastomer according to an embodiment of the present invention and fibronectin.
Figure 15:
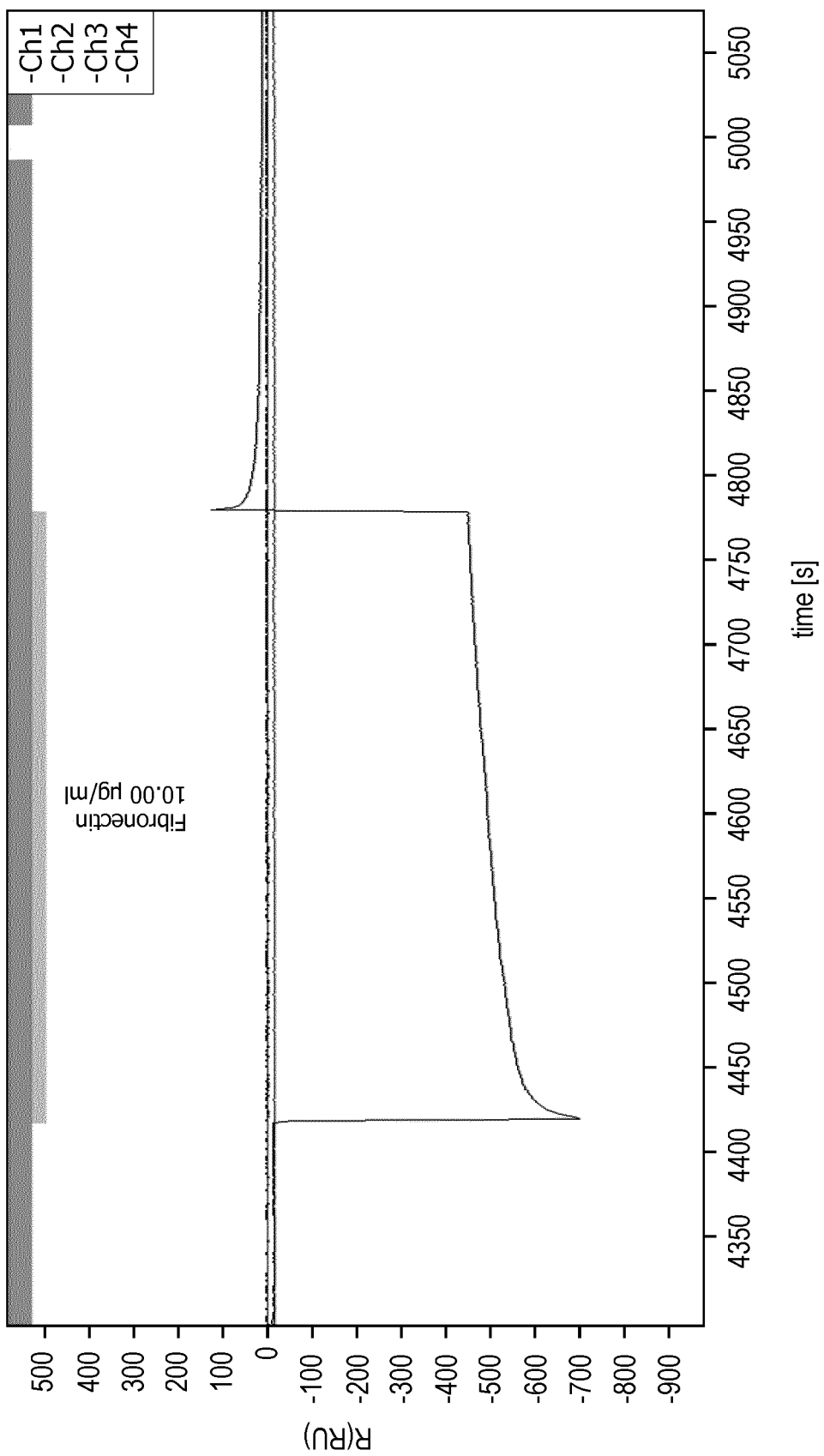

FIG. 14 depicts a surface plasmon resonance (SPR) spectrum of a fluidic device 200 comprising a fluidic device module 100 made of polybutadiene cross-linked with linoleic acid, which modified polybutadiene was reacted with EDC and NHS as described above and the resultant structure was reacted with fibronectin. As can be clearly seen from the SPR spectrum, the fibronectin is bound to the surface of the modified polybutadiene, thereby indicating that such a bulk-modified elastomer can be successfully converted into a cell-culturing scaffold. FIG. 15 shows the part of the SPR spectrum of FIG. 14 in which this surface modification is clearly shown. As can be seen the SPR baseline is shifted by approximately 2,000 RU, thus clearly indicating the binding of the fibronectin to the linoleic acid-modified polybutadiene. What is more, the SPR spectrum remained stable under the fluid streams (flushing) to which the fluidic device 200 was exposed, thereby further demonstrating that the linoleic acid is (covalently) bound to the polybutadiene, as no linoleic acid was washed away during this procedure. As expected, strongest covalent binding between the fibronectin and the material of the present invention was observed at the highest concentration of fibronectin (i.e. the chip in channel 4).

Next, binding of cell lines MDA-MB231 and MCF-7 to the chip of channel 4 was investigated to demonstrate the ability of the covalently bound fibronectin to bind to such cell lines. To this end, the above described SPR procedure was repeated with fresh chips in channels 2-4 (channel 1 being used as a reference again), over which 60 µl of 10 µg/ml Fibronectin at a flow rate of 10 µl/min at a dissociation time of 1 s was run to coat the surfaces of the fresh chips with fibronectin. After the surfaces were recoated with fibronectin cells, $2*10^6$ cells/ml of MDA-MB231 were flowed across channel 2 in 4 injection steps of 200 µl, at a flow rate of 10 µl/min and a dissociation time set to the maximum of 1800 s to give the cells enough time to bind to the fibronectin. The same was done for channel 4 with $1.3*10^6$ cells/ml of the cell line MCF-7 in 4 injection steps of 200 µl. In total, cells were given almost 2 hours to bind to the chip surface. The cells subsequently were exposed to 200 µl running buffer PBS with 0.05% Tween that was injected over channels 1-4 at a flow rate of 10 µl/min and the maximum dissociation time to flush away any cells not bonded to the chip surfaces. Bonded cells were removed from the chip surfaces with an injection of 200 µl 0.25% trypsin 0.25% over channel 1, 2, 3 and 4 at a flow rate of 10 µl/min and the maximum dissociation time.

After each experiment, the SPR machine was cleaned by flushing the system with 70% ethanol, sanitized with 1-2% hypochlorite and desorbed with 0.5% SDS, 50 mM glycine-NaOH (pH 9.5) to reduce contaminants or other build-up of dirt in the system.

Figure 16:
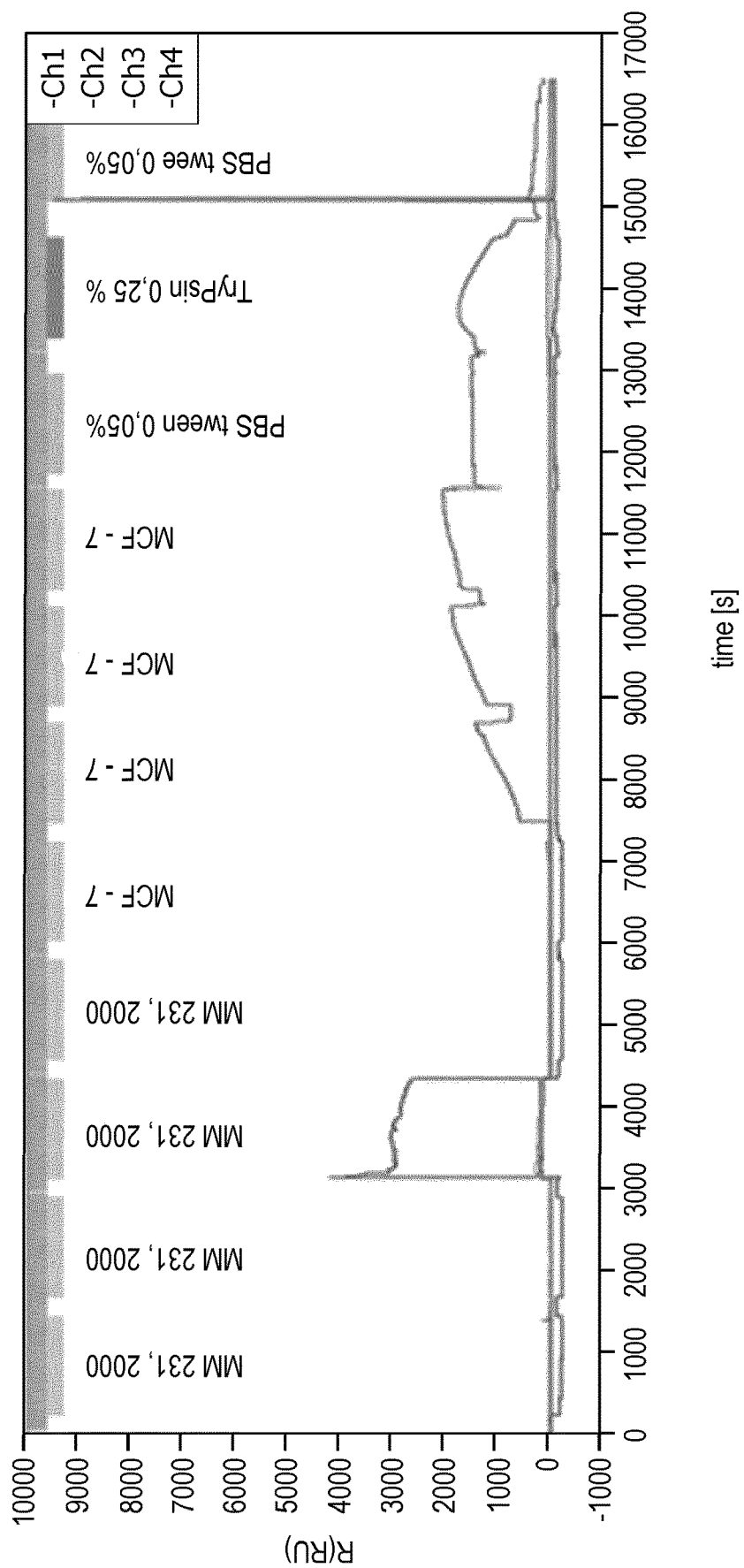
FIG. 16 depicts a SPR spectrum of a binding reaction between a bulk-modified elastomer according to an embodiment of the present invention to which fibronectin is bound and human tissue cells.

FIG. 16 depicts a SPR spectrum of the fibronectin-bound linoleic acid-modified polybutadiene-based fluidic device 200 after seeding the device with cells from MDA-MB 231 and MCF-7 cell lines. It can be seen that these cell lines attached to the fibronectin bound to the linoleic acid-modified polybutadiene. The cells remained attached to the fluidic device 200 whilst flushing the device with a running buffer but could be cleaved off by the trypsin solution. This therefore clearly demonstrates that the cells effectively bind to the device membrane, with the fibronectin being covalently bound to the membrane surface as the fibronectin (and bound cells) are not washed away by the running buffer.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A material for binding to a cell culturing protein, the material comprising:
a bulk-modified elastomer,
wherein the bulk-modified elastomer comprises a plurality of fatty acid moieties covalently bound to the elastomer bulk,
wherein the plurality of fatty acid moieties includes a first group and a second group,
wherein the first group of the fatty acid moieties is disposed internally within the bulk of the bulk-modified elastomer, and
wherein carboxylic acid groups of the second group of the fatty acid moieties are available at a surface of the bulk-modified elastomer to provide the binding to the cell culturing protein.

2. The material of claim 1, wherein at least some of the fatty acid moieties are covalently bound to the elastomer bulk through cross-links between a vinyl or hydride functional group of the elastomer and a carbon-carbon bond of the fatty acid moieties.

3. The material of claim 1, wherein at least some of the fatty acid moieties are covalently bound to the elastomer bulk through a cross-linking reaction between a vinyl or hydride functional group of the elastomer and an unsaturated carbon-carbon bond of an unsaturated fatty acid, wherein the unsaturated fatty acid is selected from the group consisting of myristoleic acid, palmitoleic acid, sapienic acid, oleic acid, elaidic acid, vaccenic acid, linoleic acid, linoeladic acid, α-linolenic acid, arachidonic acid, eicospaentaenoic acid, erucic acid and docosahexaenoic acid.

4. The material of claim 1, wherein the elastomer comprises a polybutadiene backbone or a silicone backbone.

5. The material of claim 4, wherein at least a fraction of the carboxylic acid groups within the silicone backbone is saponified.

6. A cell culturing scaffold comprising the material of claim 1 and a cell culturing protein bound to at least some of the carboxylic acid groups.

7. The cell culturing scaffold of claim 6, wherein the protein is selected from the group consisting of fibronectin, collagen and elastin.

8. A fluidic device comprising a flow channel,
wherein the flow channel extends over a membrane,
wherein the membrane comprises the material of claim 1.

9. The fluidic device of claim 8, further comprising:
a first major surface,
wherein the first major surface comprises a first recessed structure, wherein the first recessed structure defines a first flow channel; and
a second major surface,
wherein the second major surface opposes the first major surface,
wherein the second major surface comprises a second recessed structure,
wherein the second recessed structure defines a second flow channel,
wherein the membrane separates the first flow channel from the second flow channel.

10. The fluidic device of claim 8, wherein the fluidic device is a monolithic fluidic device.

11. The fluidic device of claim 8, further comprising a pair of cover plates, wherein the pair of cover plates are arranged to fluidly seal the fluidic device.

12. The fluidic device of claim 11,
wherein the pair of cover plates comprise a first cover plate and a second cover plate,
wherein the first cover plate covers the first major surface, thereby sealing the first fluidic channel,
wherein the second cover plate covers the second major surface, thereby sealing the second fluidic channel.

13. The material of claim 1, wherein the carboxylic acid groups are homogeneously distributed across a surface of the material.

14. The cell culturing scaffold of claim 6, wherein the cell culturing scaffold has a homogeneous distribution of the cell culturing protein across a surface of the bulk-modified elastomer.

15. A material for binding to a cell culturing protein, the material comprising:
a bulk-modified elastomer,
wherein the bulk-modified elastomer comprises a plurality of fatty acid moieties covalently bound to the elastomer bulk,
wherein the plurality of fatty acid moieties includes a first group and a second group,
wherein the first group of the fatty acid moieties is disposed internally within the bulk of the bulk-modified elastomer,
wherein at least some of the fatty acid moieties are covalently bound to the elastomer bulk through a cross-linking reaction between a vinyl or hydride functional group of the elastomer and an unsaturated carbon-carbon bond of an unsaturated fatty acid, and
wherein carboxylic acid groups of the second group of the fatty acid moieties are available on an external surface of the material to provide the binding to the cell culturing protein.

16. The material of claim 15, wherein the material is suitable for inclusion in a cell culturing scaffold in which the cell culturing protein is bound to at least some of the carboxylic acid groups.

17. The material of claim 15, wherein the carboxylic acid groups are homogeneously distributed across a surface of the material.

18. A material for binding to a cell culturing protein, the material comprising:
a bulk-modified elastomer,
wherein the bulk-modified elastomer comprises:
a molded elastomer bulk, and
a plurality of fatty acid moieties covalently bound to the molded elastomer bulk,
wherein the plurality of fatty acid moieties includes a first group and a second group,
wherein the first group of the fatty acid moieties is disposed internally within the molded elastomer bulk, and
wherein carboxylic acid groups of the second group of the fatty acid moieties are available to provide the binding to the cell culturing protein.

19. The material of claim 18, wherein the material is suitable for inclusion in a cell culturing scaffold in which the cell culturing protein is bound to at least some of the carboxylic acid groups.

20. The material of claim 18, wherein the carboxylic acid groups are homogeneously distributed across a surface of the material.

* * * * *